United States Patent [19]

Gubin et al.

[11] Patent Number: 5,444,056

[45] Date of Patent: Aug. 22, 1995

[54] AMINOALKOXYPHENYL DERIVATIVES, PROCESS FOR THEIR PREPARATION AND COMPOSITIONS CONTAINING THEM

[75] Inventors: Jean Gubin; Pierre Chatelain; Henri Inion, all of Brussels; Gilbert Rosseels, Emmel, all of Belgium

[73] Assignee: Sanofi, Paris, France

[21] Appl. No.: 476,342

[22] Filed: Feb. 7, 1990

[30] Foreign Application Priority Data

Feb. 7, 1989 [FR] France .................. 89 01554

[51] Int. Cl.$^6$ .................. C07D 221/02; A61K 31/33
[52] U.S. Cl. .................. 514/18.3; 514/213; 514/300; 514/307; 540/461; 540/523; 546/112; 546/148; 546/183
[58] Field of Search .................. 546/183, 148, 112; 514/300, 213, 307, 183; 540/523, 461

[56] References Cited

U.S. PATENT DOCUMENTS

| | | | |
|---|---|---|---|
| 3,859,305 | 1/1975 | Posselt et al. | 548/492 |
| 3,860,609 | 1/1975 | Lundt | 548/484 |
| 3,947,470 | 3/1976 | Brenner et al. | 549/468 |
| 3,991,060 | 11/1976 | Curran | 546/183 X |
| 4,103,012 | 7/1978 | Gubin et al. | 546/112 |
| 4,117,128 | 9/1978 | Brenner | 544/376 |
| 4,379,167 | 4/1983 | Lunsford et al. | 424/330 |
| 4,499,095 | 2/1985 | Rosseels et al. | 514/299 |
| 4,654,360 | 3/1987 | Greenhouse et al. | 514/418 |
| 4,675,405 | 6/1987 | Musser et al. | 546/172 |
| 4,826,847 | 5/1989 | Michel et al. | 514/256 |

FOREIGN PATENT DOCUMENTS

| | | |
|---|---|---|
| 0235111 | 9/1987 | European Pat. Off. . |
| 0302792 | 9/1987 | European Pat. Off. . |
| 0287696 | 10/1988 | European Pat. Off. . |
| 23141578 | 9/1977 | France . |

OTHER PUBLICATIONS

Alfred Burger, Chemical Structure and Biological Activity, pp. 64–80, 1980.
Chemical Abstracts, vol. 109, p. 606, 1988.
Journal of Medicinal Chemistry, vol. 21, No. 2, Feb. 1978, American Chemical Society, Washington, D.C.;

M. T. Cox et al.: "Linked aryl aryloxypropanolamines as a new class of lipid catabolic agents", pp. 182–188.

*Primary Examiner*—Johann Richter
*Assistant Examiner*—Catherine Scalzo
*Attorney, Agent, or Firm*—Jacobson, Price, Holman & Stern

[57] ABSTRACT

An aminoalkoxyphenyl derivative of general formula:

$$Cy-B-Ph-O-A-Am \qquad (1)$$

as well as a pharmaceutically acceptable salt thereof in which
B represents a —S—, —SO— or —SO$_2$— group,
Ph represents an optionally substituted phenyl radical,
A denotes a straight or branched alkylene radical having from 2 to 5 carbon atoms or a 2-hydroxy propylene radical in which the hydroxy is optionally substituted by a C$_1$–C$_4$ alkyl radical.
Am represents a group:

(F)

$$-N\begin{pmatrix}R_3 \\ R_4\end{pmatrix}$$

or (G)

$$-N\begin{pmatrix}R_4 \\ (CH_2)_n \\ (CH_2)_m\end{pmatrix}\begin{pmatrix}R_5 \\ R'_5 \\ R''_5\end{pmatrix}$$

or (Abstract continued on next page.)

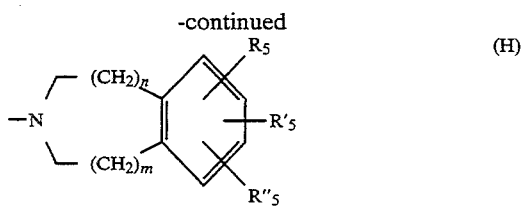
and Cy is a cyclic group, provided that when Cy represents either a benzo[b]furyl group substituted at position 4 by a halogen atom or a $C_1$-$C_4$ alkyl group, or a benzo[b]thienyl group substituted at position 4 by a halogen atom or by a $C_1$-$C_4$ alkyl group and when B represents a —$SO_2$— group, $R_3$ represents a —Alk—Ar radical.
22 Claims, No Drawings

AMINOALKOXYPHENYL DERIVATIVES, PROCESS FOR THEIR PREPARATION AND COMPOSITIONS CONTAINING THEM

The present invention relates, in a general manner, to new cyclic derivatives, and more particularly, to new aminoalkoxyphenyl derivatives as well as to a process for their preparation.

More particularly, the new aminoalkoxyphenyl derivatives of the invention can be represented by the general formula:

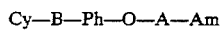

Cy—B—Ph—O—A—Am  (1)

in which:

B represents a —S—, —SO—, —SO$_2$— group,
Ph represents a radical of formula:

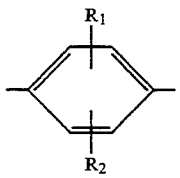

(D)

or

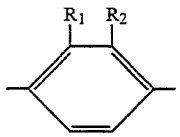

(E)

$R_1$ and $R_2$, which are identical or different, each denotes hydrogen, a methyl or ethyl radical or a halogen such as chlorine, bromine or iodine, A denotes a straight or branched alkylene radical having 2 to 5 carbon atoms or a 2-hydroxypropylene radical in which the hydroxy is optionally substituted by a lower alkyl radical, Am represents a group:

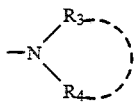

(F)

or

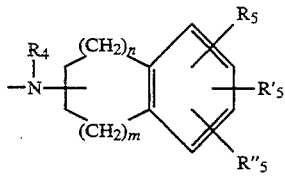

(G)

or

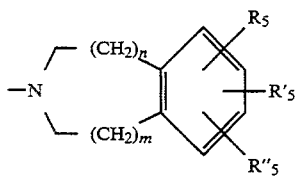

(H)

in which:

$R_3$ denotes an alkyl or cycloalkyl radical or a radical of formula:

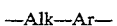

—Alk—Ar— in which

Alk denotes a simple bond or a linear or branched alkylene radical having from 1 to 5 carbon atoms and Ar denotes a pyridyl, phenyl, 2,3-methylenedioxyphenyl or 3,4 methylenedioxyphenyl radical or a phenyl group substituted by one or more substituents, identical or different, selected from halogen atoms, lower alkyl groups or lower alkoxy groups, $R_4$ denotes hydrogen, an alkyl radical, or $R_3$ and $R_4$, when they are taken together, represent an alkylene or alkenylene radical having from 3 to 6 carbon atoms and optionally substituted by a phenyl radical or optionally interrupted by —O—, —N= or —N—$R_6$, $R_6$ representing hydrogen, a lower alkyl radical, a cycloalkyl radical, a phenyl radical optionally substituted by a halogen atom or by a lower alkyl or lower alkoxy group, $R_5$, $R'_5$ and $R''_5$, which are identical or different, each denotes hydrogen, a halogen atom such as chlorine or bromine, a lower alkyl group or a lower alkoxy group, n and m, identical or different, each denotes 0, 1, 2 or 3, Cy represents one of the groups of formula

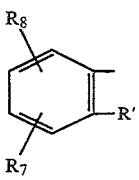

(I)

or

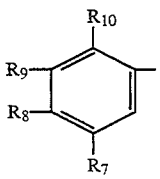

(I')

or

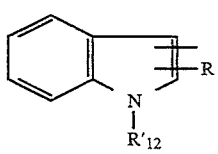

(K')

or

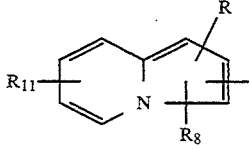

(J)

or

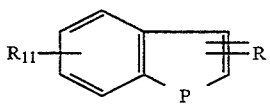

(K)

or

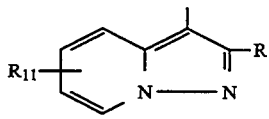 (L)

or

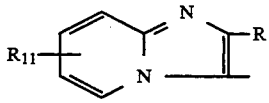 (M)

or

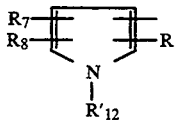 (N)

or

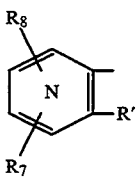 (Q)

or

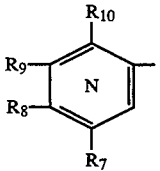 (Q')

in which:
- R represents hydrogen, an alkyl radical, a cycloalkyl radical, a benzyl radical or a phenyl radical optionally substituted by one or several substituents, which may be identical or different, selected from halogen atoms, for example fluorine, chlorine or bromine or from lower alkyl, lower alkoxy or nitro groups,
- R' represents an alkyl radical, a cycloalkyl radical, a benzyl radical or a phenyl radical optionally substituted by one or several substituents, which may be identical or different, selected from halogen atoms or from lower alkyl, lower alkoxy or nitro groups,
- $R_7$, $R_8$ and $R_9$, identical or different, each represents hydrogen, a lower alkyl radical, a lower alkoxy radical, a halogen atom such as chlorine or bromine, a hydroxy, benzyloxy, nitro, amino, lower alkylamino, lower dialkylamino, sulfonamido, lower alkylsulfonamido, phenylsulfonamido, cyano, lower alkoxycarbonyl or lower alkylcarbonyl group,
- $R_{10}$ represents hydrogen, a lower alkoxy radical, a halogen atom, a hydroxy, benzyloxy, nitro, amino, lower alkylamino, lower dialkylamino, sulfonamido, lower alkylsulfonamido, phenylsulfonamido, cyano, lower alkoxycarbonyl or lower alkylcarbonyl group, provided that:
  the $R_7$ and $R_8$ groups, on the one hand, and $R_7$, $R_8$, $R_9$ and $R_{10}$, on the other never simultaneously represent hydrogen, and that the radical (I) or (I') do not represent a mono-halophenyl radical;
- $R_{11}$ represents a lower alkyl radical, a lower alkoxy radical, a halogen atom, a hydroxy, benzyloxy, nitro, amino, lower alkylamino, lower dialkylamino, sulfonamido, lower alkylsulfonamido, phenylsulfonamido, cyano, lower alkoxycarbonyl or lower alkylcarbonyl group.
- P denotes a heteroatom or a heterogroup selected from —O—, —S—, and —N—$R_{12}$ in which $R_{12}$ represents hydrogen, a lower alkyl, cycloalkyl, benzyl or halogenobenzyl group, a —A—Am group as defined above, a lower alkylsulfonyl group or a phenylsulfonyl group optionally substituted by one or several halogen atoms or lower alkyl or lower alkoxy groups,
- $R'_{12}$ represents a —A—Am group as defined above an alkylsulfonyl group optionally substituted by one or several halogen atoms, or lower alkyl or lower alkoxy groups, provided that when Cy represents either a benzo[b]furyl group substituted at position 4 by a halogen atom or by a lower alkyl group, or a benzo[b]thienyl group substituted at position 4 by a halogen atom or by a lower alkyl group and, when B represents a —$SO_2$— group, $R_3$ represents a —Alk—Ar radical.

In the present context, both in the description and in the Claims, the following meaning attaches to the terms stated above:
- "alkyl" denotes saturated aliphatic hydrocarbon residues having up to 8 carbon atoms such as methyl, ethyl, n-propyl, isopropyl, n-butyl, isobutyl, tert-butyl, n-pentyl, neopentyl, n-hexyl, n-heptyl or n-octyl,
- "lower alkyl" denotes saturated aliphatic hydrocarbon residues having up to 4 carbon atoms such as methyl, ethyl, n-propyl, isopropyl, n-butyl, isobutyl, tert-butyl or 1-methylpropyl,
- "lower alkoxy" denotes a hydroxy group substituted with a lower alkyl group as defined above,
- "cycloalkyl" denotes an alicyclic group having from 3 to 6 carbon atoms, such as cyclopropyl or cyclohexyl.

Thus, taking into account the meanings given above:
- R or R' can denote, in particular, a methyl, ethyl, n-propyl, isopropyl, n-butyl, isobutyl, tert-butyl, 1-methylpropyl, n-pentyl, neopentyl, phenyl, monofluoro-, monochloro- or monobromo-phenyl, difluoro-, dichloro- or dibromo-phenyl, monomethyl- or dimethylphenyl, monomethoxy- or dimethoxy-phenyl, radical or a methylphenyl radical substituted by a halogen atom.
- A can denote, in particular, a 1,2-ethylene, 1,3-propylene, 2-methyl-1,3-propylene, 1,4-tetramethylene or 1,5-pentamethylene chain.
- $R_3$ can denote, in particular, a methyl, ethyl, n-propyl, isopropyl, n-butyl, isobutyl, tert-butyl, 1-methylpropyl, n-pentyl, n-hexyl, n-heptyl, n-octyl, phenyl, benzyl, phenethyl, methoxyphenyl, dimethoxy phenethyl, for example 3,4-dimethoxyphenethyl, dimethylphenethyl, dimethoxybenzyl or pyridylethyl radical or a phenethyl radical substituted in the aromatic ring by methyl and methoxy radicals, R4 can denote, in particular, a methyl, ethyl, n-propyl, isopropyl, n-butyl, isobutyl, tert-butyl, n-pentyl, neopentyl, n-hexyl, n-heptyl or n-octyl radical, R3 and R4, taken together, can denote, in particular, a 1,4-tetramethylene, 1,5-pentamethylene, 3-oxo-1,5-pentamethylene, 3-aza-1,5-pentamethylene, 3-methylaza-1,5-pentamethylene, 3-phenylaza-1,5-pentamethylene, or —CH=CH—N=CH— such that R3 and R4, taken together with the nitrogen atom to which they are attached, can denote, in particular, a pyrrolidinyl, piperidinyl, morpholinyl, piperazinyl, 4-methyl piperazinyl, 4-phenyl piperazinyl or 1H-imidazolyl radical.

R5, R'5 and R''5 can denote, in particular, a methyl or methoxy radical or a chlorine atom, R7, R8, R9, R10 and R11 can denote, in particular, a methyl, ethyl, methoxy or ethoxy radical, a chlorine atom, a methylsulfonamido, ethylsulfonamido, methylamino, ethylamino, dimethylamino, diethylamino, methoxycarbonyl, ethoxycarbonyl, methylcarbonyl or ethylcarbonyl group.

A special class of compounds of formula (1) is constituted by those in which Cy represents an indolizinyl group.

Another class of compounds of formula (1) is represented by those in which R1 and R2 each denotes hydrogen.

Another class of compounds of formula (1) is formed by those compounds in which R3 represents a —Alk—Ar radical or R3 represents hydrogen and R4 represents tert-butyl or R3 and R4 each represents n-propyl or n-butyl. A class of compounds of formula (1) is represented by those compounds in which the chain

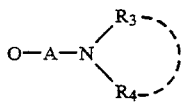

represents a [N-methyl N(3,4-dimethoxy-β-phenethyl)amino]propoxy or [N-methyl N-(3,5-dimethoxy-β-phenethyl)amino]propoxy group.

Other particularly useful compounds of formula (1) are those in which R represents an isopropyl or cyclopropyl group.

The invention also relates to the pharmaceutically acceptable salts of the compounds of formula (1) formed with an organic or inorganic acid.

As examples of organic salts of this type, there may be mentioned the oxalate, maleate, fumarate, methanesulfonate, benzoate, ascorbate, pamoate, succinate, hexamate, bismethylenesalicylate, ethanedisulfonate, acetate, propionate, tartrate, salicylate, citrate, gluconate, lactate, malate, cinnamate, mandelate, citraconate, aspartate, palmitate, stearate, itaconate, glycolate, p-aminobenzoate, glutamate, benzenesulfonate and theophyllineacetate, as well as the salts formed with an amino acid such as lysine or histidine.

As examples of inorganic salts of this type, the hydrochloride, hydrobromide, sulfate, sulfamate, phosphate and nitrate may be mentioned.

The compounds of formula (1) can exist, in some cases, in the form of optical isomers, in particular as a result of the asymmetric carbon present when A represents a 2-hydroxypropylene chain.

The invention relates, at the same time, to all of the isomers of the compounds of formula (1), isomers considered in the dextrorotatory or laevorotatory form or, in the form of a mixture, for example, in the form of a racemic mixture.

It has been found that the compounds of the invention possess exceptional pharmacological properties, in particular calcium transport inhibitory properties, as well as bradycardiac, hypotensive and antiadrenergic properties.

From this point of view, the preferred compounds of the invention are those in which B represents a —SO2— group.

These properties are capable of making the compounds in question very useful in the treatment of certain pathological syndromes of the cardiovascular system, in particular in the treatment of angina pectoris, hypertension, arrhythmia and cerebral circulatory insufficiency.

Similarly, it will be possible to use the compounds of the invention alone or in combination with an anti-inflammatory agent to reduce and/or control excessive intraocular pressure. For this purpose, it will be possible to use the compounds of the invention for the treatment of ocular diseases, in particular in the treatment of glaucoma.

Generally, from 5 ng to 0.5 mg of active principle according to the invention will be administered to each eye, the daily frequency of administration depending on the gravity of the disease to be treated.

In the antitumour field, the compounds of the invention will be useful as potentiators of anticancer drugs.

Consequently, the invention also relates to pharmaceutical or veterinary compositions containing, as active principle, at least one compound of formula (1) or a pharmaceutically acceptable salt of this compound, in combination with a pharmaceutical vehicle or a suitable excipient.

Depending on the route of administration selected, the daily dosage for a human being weighing 60 kg will be between 2 and 500 mg of active principle.

The compounds of the invention may be obtained as follows:

I.—When R7, R8, R9 and R10 represent hydrogen, a lower alkyl, or lower alkoxycarbonyl or lower alkylcarbonyl group and R11 has lower alkoxy group, a halogen atom, a benzyloxy, nitro, cyano, the same meaning as R7 above with the exception of hydrogen.

A.—The compounds of formula (1) in which B represents a —S— or —SO2— group and A represents an alkylene radical can be prepared, according to the invention, by condensing, in the presence of an acid acceptor and in a polar solvent such as dimethylsulfoxide or an alcohol, for example butanol, or a ketone such as methyl ethyl ketone, or a non-polar solvent such as an aromatic hydrocarbon, for example benzene, toluene or xylene, a 4-alkoxyphenyl derivative of general formula:

Cy—B'—Ph—O—Ax     (2)

in which B' represents a —S— or —SO2— group, Cy and Ph have the same meaning as above, A represents an alkylene radical as defined in formula (1) and X represents a halogen atom, preferably bromine, or an alkylsulfonyloxy group having from 1 to 4 carbon atoms such as, for example, methanesulfonyloxy, or an arylsulfonyloxy group having from 6 to 10 carbon atoms, such as benzenesulfonyloxy or p-toluenesulfonyloxy, with an amine of general formula:

H—Am (3)

in which Am has the same meaning as above, to form the required derivative of formula (1) in the form of the free base.

Generally, the condensation in question is performed at a temperature between room temperature and the reflux temperature of the medium, the acid acceptor being, for example, an alkali metal carbonate or hydroxide or an excess of amine of formula (3).

The compounds of formula (2) in question can be obtained:

a) When X is a halogen, by condensation of a 4-hydroxyphenyl derivative of general formula:

Cy—B'—Ph—OH (4)

in which Cy, B' and Ph have the same meaning as above, with a dihaloalkane of general formula:

Hal—A—Hal (5)

in which A denotes an alkylene radical as defined in the formula (1) and Hal denotes a halogen atom, preferably bromine, this reaction being performed at reflux in a solvent such as methyl ethyl ketone or N,N-dimethylformamide and in the presence of a basic agent such as an alkali metal carbonate, for example potassium carbonate, an alkali metal hydride such as sodium hydride, an alkali metal hydroxide, for example sodium or potassium hydroxide, or an alkali metal alcoholate, for example sodium methylate or ethylate, b) when X represents an alkylsulfonyloxy or arylsulfonyloxy group, by condensation of a halide of general formula:

Hal—W in which W represents an alkylsulfonyl radical having from 1 to 4 carbon atoms, for example methanesulfonyl or an arylsulfonyl radical having from 6 to 10 carbon atoms, for example benzenesulfonyl or p-toluenesulfonyl, in an acid acceptor solvent, for example pyridine, with a 4-hydroxyalkoxy derivative of general formula:

Cy—B'—Ph—O—A—OH (6)

in which Cy, B' and Ph have the same meaning as above and A denotes an alkylene radical as defined in formula (1).

As regards the compounds of formula (6), these latter can be prepared by condensing, in a suitable solvent such as N,N-dimethylformamide and in the presence of a basic agent such as an alkali metal carbonate, for example potassium carbonate, an alkali metal hydroxide such as sodium or potassium hydroxide, an alkali metal hydride such as sodium hydride or an alkali metal alcoholate, for example sodium methylate or ethylate, a hydroxy-phenyl derivative of formula (4) above with a halogenated alcohol of general formula:

Hal—A—OH (7)

in which A represents an alkylene radical as defined in the formula (1) and Hal has the same meaning as above.

The amines of formula (3) are known compounds. For example, amines covered by the formula (3) have been described in the European patent applications Nos. 219.813, 227.986 and 235.111 or can be prepared according to the methods described therein.

Similarly, some compounds of formula (4) are known compounds, for example those in which Cy represents a benzofuryl or benzothienyl group, these groups being unsubstituted or substituted at position 4 by a halogen atom or a lower alkyl group and B' represents —$SO_2$. These compounds are disclosed in the U.S. Pat. No. 4,117,128. Generally, the other compounds of formula (4) can be prepared by adapting to the required compound the method described in the above-mentioned U.S. patent or standard methods such as those described hereunder.

In most cases, the compounds of formula (4) can be obtained by fixing a 4-protected benzenesulfonyl or phenylthio chain to the appropriate carbocycle or heterocycle using a Friedel-Crafts reaction and by deprotecting the oxygen in the 4-position of the benzenesulfonyl or phenylthio group by means of procedures known to regenerate the hydroxyl group.

Hereunder are described examples of methods which can be commonly used to prepare such compounds of formula (4).

a) Compounds of formula (4) in which Cy represents a radical of formula (1) or (1').

In order to obtain such compounds in which B represents a —$SO_2$— group, it is possible, for example, to use the method described in Communications, April 1984 p. 323, which consists of reacting a benzene derivative of general formula:

(8)

or

(8')

in which R' has the same meaning as above and $R'_7$, $R'_8$, $R'_9$ and $R'_{10}$ denote hydrogen, a lower alkyl radical, a lower alkoxy radical, a halogen atom, a benzyloxy, nitro, cyano, lower alkoxycarbonyl or lower alkylcarbonyl group, with a sulfonate derivative of general formula:

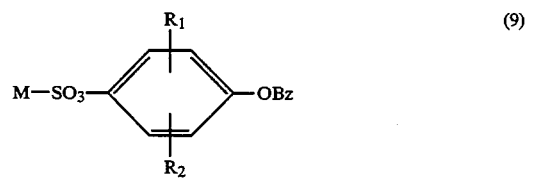

(9)

in which $R_1$ and $R_2$ have the same meaning as above, M represents an alkali metal atom, for example sodium, and Bz represents a benzyl radical, in the presence of methanesulfonic acid and phosphoric anhydride, to give the derivatives of general formula:

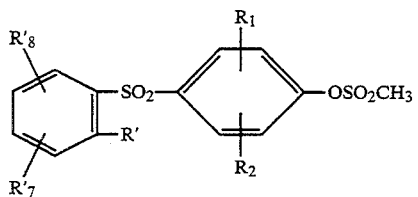 (10)

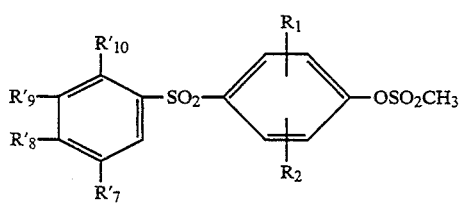 (10')

in which $R'$, $R_1$, $R_2$, $R'_7$, $R'_8$, $R'_9$ and $R'_{10}$ have the same meaning as above, which derivatives are hydrolysed in the presence of a basic agent such as an alkali metal hydroxide, for example sodium hydroxide, to form the required compounds of formula (4).

b) Compounds of formula (4) in which Cy presents a radical of formula (J)

Generally speaking, such compounds can be obtained by adapting known methods, for example those described in the European patent application No. 235.111, the British patent No. 1.174.124, Berichte 60, p. 1607 (1927), Austr. J. Chem. 25, p. 1549 (1972), Khim. Geterotsikl. Soedin. 1972 No. 9 or 1976, No. 4, 506–510, J.A.C.S. 81, 1456 (1959) or C.A. 84, 179888 (1976).

For example, compounds of formula (4) in which Cy represents a 2-R-indolizin-1-yl group can be prepared by reacting a pyridine derivative of general formula:

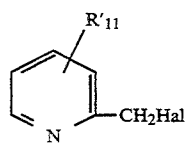 (11)

in which $R'_{11}$ represents a lower alkyl radical a lower alkoxy radical a halogen atom, a benzyloxy, nitro, cyano, lower alkoxycarbonyl or lower alkylcarbonyl group and Hal represents a halogen atom, for example chlorine, with a derivative of general formula:

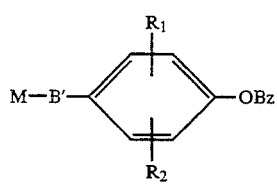 (12)

in which Bz, $R_1$, $R_2$, B' and M have the same meaning as above, to form a compound of general formula:

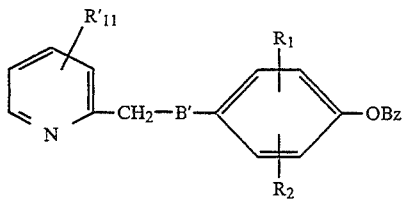 (13)

in which B', $R_1$, $R_2$, $R'_{11}$ and Bz have the same meaning as above.

The compound of formula (13) is then treated with a ketone of general formula:

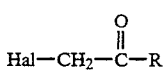 (14)

in which R and Hal have the same meaning as above, to form the indolizine derivatives of general formula:

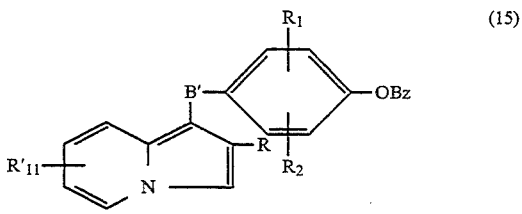 (15)

in which B', R, $R_1$, $R_2$, $R'_{11}$ and Bz have the same meaning as above. These derivatives of formula (15) are then reacted with ammonium formate in the presence of palladium on charcoal, which gives the required compounds of formula (4), which compounds can, if necessary, be reacted, for example, with a suitable agent capable of generating an electrophilic group in order to form compounds of formula (4) in which $R_8$ is at position 3 and is other than hydrogen.

Similarly, compounds of formula (4) in which Cy represents a 2-R-indolizin-2-yl group can be obtained by reacting an indolizine derivative of general formula:

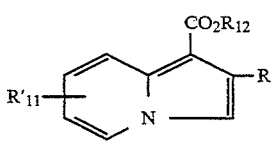 (16)

in which $R'_{11}$ has the same meaning as above and $R_{12}$ represents a lower alkyl group, for example ethyl, with a halide of general formula:

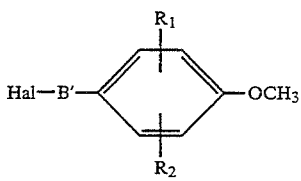 (17)

in which B', $R_1$, $R_2$ and Hal have the same meaning as above, and in the presence of a Friedel-Crafts catalyst such as aluminium chloride, to form the compound of general formula:

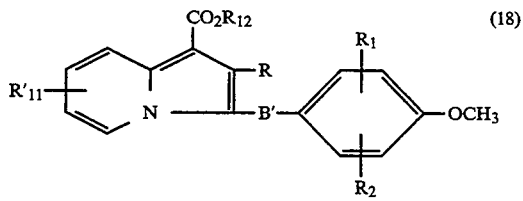

in which B', R, R$_1$, R$_2$, R'$_{11}$ and R$_{12}$ have the same meaning as above. The compound of formula (18) is then demethylated by means of an ethanethiol-/aluminium chloride mixture, which provides the 4-methoxy phenyl derivatives of general formula:

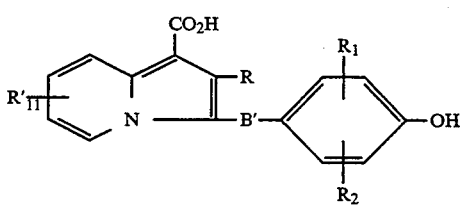

in which B', R, R$_1$, R$_2$ and R$_{11}$ have the same meaning as above, which compounds provide the required compounds of formula (4) after being heated at about 200° C.

The compounds of formula (16) are either known compounds having been published in J. Chem. Soc. 1962, pp. 2627–2629, or compounds which can be prepared by the method described therein.

c) Compounds of formula (4) in which Cy represents a radical of formula (K) or (K').

These compounds can be prepared by adapting the method described in the U.S. Pat. No. 4,117,128.

However, they can also be prepared in accordance with the method described below:

1) Cy represents a radical of formula (K) in which P represents —O—, —S— or —NH:

by reacting a compound of general formula:

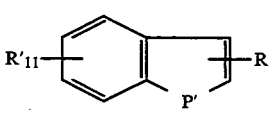

in which R and R'$_{11}$ have the same meaning as above and P' denotes —O—, —S— or —NH, with a compound of general formula:

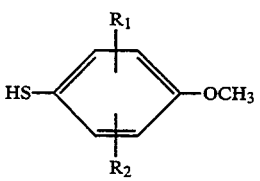

in which R$_1$ and R$_2$ have the same meaning as above, the reaction being performed in the presence of iodine to give the compound of general formula:

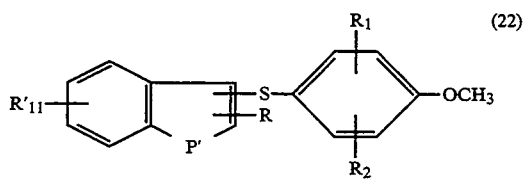

in which R$_1$, and R$_2$, P' and R'$_{11}$ have the same meaning as above, which, after oxidation with 3-chloroperbenzoic acid, gives the compounds of general formula:

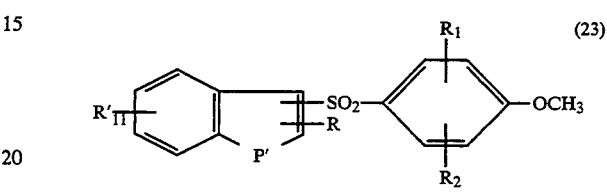

in which R, R$_1$, R$_2$, R'$_{11}$ and P' have the same meaning as above. The compounds of formulae (22) and (23) can then be demethylated by means of 2-mercaptoethanol in the presence of sodium hydride to give the required compounds of formula (4).

2) Cy represents a radical of formula (K) in which P represents a —N—R$_{12}$ group in which R$_{12}$ is other than hydrogen:

by treating a compound of formula (22) or (23), in which P' represents —NH, optionally in the form of a metal derivative, with a halide of formula R$_{12}$-Hal in which Hal has the same meaning as above, for example iodine, and R$_{12}$ has the same meaning as above with the exception of hydrogen and by demethylating the derivative substituted at position 1 thus obtained with 2-mercaptoethanol in the presence of sodium hydride to form the required compound of formula (4). The compounds of formula (20) are known products and can be prepared by known methods. For example, the indole derivatives of formula (20) can be obtained in accordance with the methods described in the French patent No. 2.117.878.

3) Cy represents a radical of formula (K'):

by adapting the method described in paragraph 2) above to the required compound.

4) Cy represents a radical of formula (N):

by adapting one of the methods described in the paragraphs 1) and 2) above to the required compound.

d) Compounds of formula (4) in which Cy represents a radical of formula (L):

In accordance with the method described in the European patent application No. 121.197, a 2-R-pyrazolo[1,5-a]pyridine of general formula:

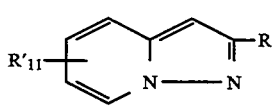

in which R and R'$_{11}$ have the same meaning as above is reacted with a halide of general formula:

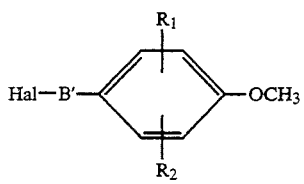

(25)

in which Hal, B', R₁ and R₂ have the same meaning as above, in the presence of a Friedel-Crafts catalyst such as aluminium chloride, to form a 4-methoxyphenyl derivative of general formula:

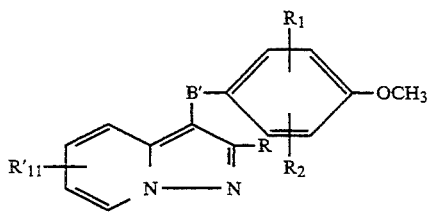

(26)

in which R, R₁, R₂, R'₁₁ and B' have the same meaning as above. The pyrazolopyridine derivative of formula (26) is then demethylated by means, for example, of pyridine hydrochloride at 200°–220° C. to provide the required compound of formula (4).

Some compounds of formula (24) are known products having been published in the U.S. Pat. No. 4,028,370. They can be obtained, for example, by adapting the method described in J. Org. Chem. 33 (10) pp. 3766–3770 or Org. Synth. 43 p. 1 (1963) to the required compound.

e) Compounds of formula (4) which Cy represents a radical of formula (M)

A 2-R-imidazo[1,2-a]pyridine of general formula:

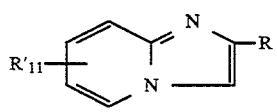

(26')

in which R and R'₁₁ have the same meaning as above is reacted with a halogen of formula (17) in the presence of a Friedel-Crafts catalyst such as aluminium chloride, to give a compound of general formula:

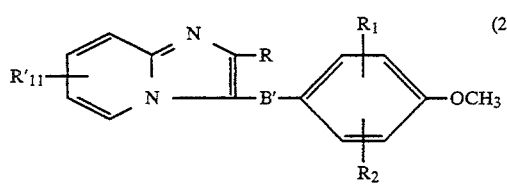

(27)

in which R, R₁, R₂, R'₁₁ and B' have the same meaning as above. The compound of formula (27) is then demethylated using an appropriate agent, for example hydrobromic acid or an ethanethiol/aluminium chloride mixture, to give the required compound of formula (4). 2-aryl-imidazo[1,2-a]pyridines are already known from J. Med. Chem. 8 p. 305 (1965). The other compounds of formula (26') can be obtained in accordance with the method described in this reference or by using standard procedures.

f) Compounds of formula (4) in which Cy represents a radical of formula (Q) or (Q')

Such pyridine derivatives can be obtained by demethylating, with a suitable agent such as aqueous hydrobromic acid, a 4-methoxyphenyl derivative of general formula:

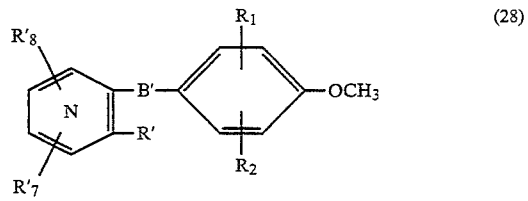

(28)

or

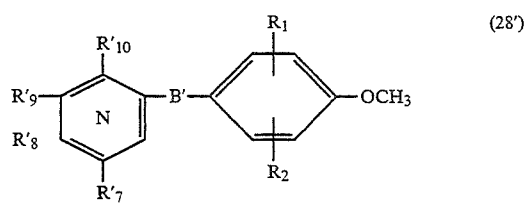

(28')

in which R', R₁, R₂, R'₇, R'₈, R'₉ and R'₁₀ have the same meaning as above, these 4-methoxyphenyl derivatives being prepared from a compound of general formula:

(29)

or

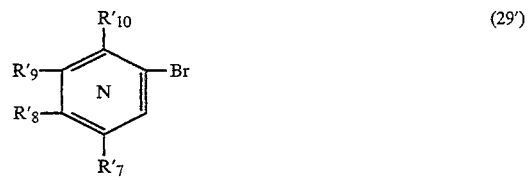

(29')

in which R, R'₇, R'₈, R'₉ and R'₁₀ have the same meaning as above, which is treated with a thiophenol derivative of general formula:

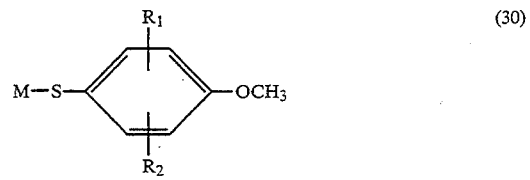

(30)

in which M, R₁ and R₂ have the same meaning as above. The compounds of formula (29) and (29') are known compounds and can be prepared according to known methods, for example by adapting the method described in Nippon Kagaku Zasshi 86 (10) pp. 1060–1067 (1967) [C.A. 16936h (1966)].

In accordance with an alternative method, the compounds of formula (1) in which B represents a —S— or —SO₂— group and A represents an alkylene radical, preferably those in which A represents a propylene radical, can also be obtained by reacting, in the presence of a basic reagent such as an alkali metal carbonate, for example potassium carbonate, an alkali metal hydroxide such as sodium or potassium hydroxide, an alkali metal hydride such as sodium hydride or an alkali metal alcoholate, for example sodium methylate or ethylate, a 4-hydroxy phenyl derivative of formula (4) above with a compound of general formula:

$$X—A—Am \quad (31)$$

in which X and Am have the same meaning as above and preferably represent chlorine or a benzenesulfonyloxy radical or a p-toluenesulfonyloxy radical and A represents an alkylene radical, the reaction taking place at reflux and in a polar solvent such as methyl ethyl ketone or dimethylsulfoxide to form the required derivative of formula (1) in the form of the free base.

The compounds of formula (31) are known products or can be prepared by known methods.

This method, when it is applied to a metal derivative of formula:

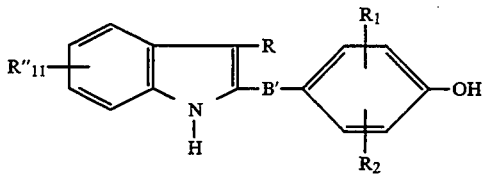

in which B′, R, $R_1$ and $R_2$ have the same meaning as above and R″$_{11}$ represents hydrogen or a group of formula R′$_{11}$ above enables indole derivatives of formula (1) in which Cy represents a (K) group in which P represents a —N—$R_{12}$— group in which $R_{12}$ represents a —A—Am group or of formula (1) in which Cy represents a (K′) group in which R′$_{12}$ represents a —A—Am group.

B.—The compounds of formula (1) in which B represents a —SO— group can be prepared by treating a sulfide of formula (1) in which B represents a —S— group with an oxidizing agent, this compound of formula (1) being in the form of the free base or of a salt so as to obtain the required derivative of formula (1) in the form of the free base or salt.

When the required compound is obtained in the form of a salt, the free base can be regenerated by treatment with a basic agent such as an alkali metal carbonate, for example potassium carbonate or an alkali metal bicarbonate, for example sodium bicarbonate.

Generally, the reaction takes place in water or in an organic solvent such as methylene chloride and in the presence of a suitable oxidizing agent such as, for example, sodium periodate, potassium permanganate or 3-chloroperbenzoic acid.

Depending on the oxidizing agent used, mixtures of sulfoxides and sulfones can be obtained. These mixtures can be separated by conventional procedures, for example by chromatography.

C.—The compounds of formula (1) in which B represents a —S— or —$SO_2$— group and A represents a 2-hydroxypropylene chain, can be obtained by reacting at reflux a derivative of formula (4) with an epihalohydrin such as epichlorhydrin or epibromhydrin in the dextrorotatory or the laevorotatory form or in the form of a mixture of these isomers, for example in the racemic form, and in the presence of a basic agent such as an alkali metal carbonate, for example potassium carbonate, an alkali metal hydroxide, for example sodium or potassium hydroxide, an alkali metal hydride such as sodium hydride or an alkali metal alcoholate, for example sodium methylate or ethylate, and in a polar solvent such as methyl ethyl ketone, to give the oxiranylmethoxy derivatives of general formula:

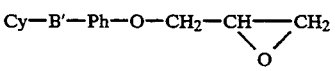

in which Cy, B′ and Ph have the same meaning as above. The oxiranylmethoxy derivatives of formula (33) are then treated at reflux with an amine of formula (3) in a polar solvent such as methyl ethyl ketone or in an excess of amine of formula (3) to give the required aminoalkoxyphenyl derivative of formula (1) in the form of the free base, in which A represents a 2-hydroxypropylene chain, which derivative can be reacted, if desired, with a lower alkyl halide in the presence of a strong base to form the compounds of formula (1) in the form of the free base, in which A represents a 2-hydroxypropylene chain in which the hydroxy is substituted by a lower alkyl radical.

In some cases, by-products may be formed in parallel with the compounds of formula (33) above, for example 4-(3-halogeno 2-hydroxy propoxy) benzenesulfonyl derivatives. On reaction with the amine of formula (3), these derivatives will nonetheless give rise to the required compounds of formula (1) in which A represents a 2-hydroxypropylene chain.

II.—When $R_7$, $R_8$, $R_9$, $R_{10}$ or $R_{11}$ represents a hydroxy group.

A compound of formula (1) in which $R_7$, $R_8$, $R_9$, $R_{10}$ or $R_{11}$ represents a benzyloxy group is hydrogenated in a suitable solvent, for example an alcohol or a ketone, and in the presence of a suitable catalyst such as Raney nickel or palladium on charcoal to give the required compound of formula (1) in the form of the free base.

III.—When $R_7$, $R_8$, $R_9$, $R_{10}$ or $R_{11}$ represents an amino, lower alkylamino or lower dialkylamino group.

A compound of formula (1) in which $R_7$, $R_8$, $R_9$, $R_{10}$ or $R_{11}$ represents a nitro group is hydrogenated in a suitable solvent, for example an alcohol or a ketone, and in the presence of a suitable catalyst, such as platinum oxide to give the required compound of formula (1) in the form of the free base, in which $R_7$, $R_8$, $R_9$, $R_{10}$ or $R_{11}$ represents an amino group, which compound can be reacted, if necessary, with an appropriate quantity of a lower alkyl halide, for example the bromide, in the presence of an alkali agent, to give the compounds of formula (1) in the form of the free base, in which $R_7$, $R_8$, $R_9$, $R_{10}$ or $R_{11}$ represents a lower alkylamino group or a lower dialkylamino group.

IV.—When $R_7$, $R_8$, $R_9$, $R_{10}$ or $R_{11}$ represents a sulfamido, lower alkylsulfamido or phenylsulfamido group.

A compound of formula (1), in which $R_7$, $R_8$, $R_9$, $R_{10}$ or $R_{11}$ represents an amino group, is reacted in a suitable solvent, for example dichloromethane, and in the presence of an acid acceptor, for example triethylamine, with a sulfonyl halide, a lower alkyl sulfonyl halide or a phenylsulfonyl halide to give the required compound of formula (1) in the form of the free base.

The compounds of formula (1) thus obtained in the form of the free base can then be converted into pharmaceutically acceptable salts by reaction with a suitable organic or inorganic acid, for example oxalic, maleic, fumaric, methanesulfonic, benzoic, ascorbic, pamoic, hexamic, bismethylenesalicylic, ethanedisulfonic, acetic, propionic, tartric, salicylic, citric, gluconic, lactic, malic, cinnamic, mandelic, citraconic, aspartic, palmitic, stearic, itaconic, glycolic, p-aminobenzoic, glutamic, benzenesulfonic, theophylline acetic acid or with lysine or histidine.

The patent FR-A-2,594,438 contains the description of 1-(4-alkylamino- or aralkylamino-alkoxy-benzenesulfonyl) indolizine derivatives endowed with active properties on the cardiovascular system, in particular calcium transport inhibitory properties and antiadrenergic properties of the α and β types. This patent covers in particular such derivatives of indolizine substituted at one of the positions 5, 6, 7 or 8 by a halogen atom, a hydroxy, lower alkyl, lower alkoxy, trifluoromethyl, nitro, cyano, carboxy, carbamoyl, lower alkoxycarbonyl or benzyloxy group.

However, none of the compounds of this type has been specifically cited or described from either the chemical or pharmacological standpoint.

It has now been surprisingly discovered that the indolozin-1-yl derivatives of formula I above, in this case 1-(4-alkylamino- or aralkylamino-alkoxy-benzenesulfonyl) indolizine derivatives substituted at position 5, 6, 7 or 8, exhibit exceptional pharmacological properties expressed in particular as calcium inhibitory and antiadrenergic properties much superior to those of the analogous derivatives unsubstituted in positions 5, 6, 7 or 8.

Similarly, alkylaminoalkoxybenzenesulfonyl-benzofuran or benzothiophene derivatives active on the cardiovascular system have been cited in the U.S. Pat. No. 4,117,128.

This patent relates to derivatives of this type comprising or not at position 5 a halogen atom or an alkyl group. Although such derivatives unsubstituted at position 5 may be considered as being actually known, nothing, a priori, permits the conclusion that the analogous compounds substituted at position 5 have really been prepared and that their pharmacological activity has actually been investigated.

In the scope of the present invention, it has been found that benzofuran derivatives analogous to those disclosed in the U.S. Pat. No. 4,117,128 but bearing a substituent on the homocycle, exhibit properties on the cardiovascular system, in particular α and β antiadrenergic properties considerably more significant than the known compounds and in particular than 2-n-butyl 3-[4-(2-diethylaminoethoxy)benzenesulfony]benzofuran.

As has been reported in detail by R. CHARLIER in "Bruxelles Médical", No. 9 September 1969, pages 543–560, it is accepted that an anti-angina drug treatment must be capable, in particular, of antagonizing the cardiovascular reactions of the adrenergic type. For this purpose, agents capable of blocking the α-receptors have been suggested.

However, the clinical application of such compounds to the treatment of angina remained unsuccessful, very probably owing to the fact that the α-receptor antagonists induce only a very partial neutralization of the adrenergic system, the activity of the β-receptors being unaffected.

Now, the most undesirable haemodynamic symptoms which occur in angina pectoris patients during painful attacks are, first and foremost, cardiac, and consequently implicate the β-receptors.

In parallel, treatments have been suggested with β-adrenergic receptor antagonists. These compounds are of genuine clinical value and diminish attacks of angina by reducing the work of the heart by slowing the heart rate. However, there is no fall in the peripheral arterial resistance which, on the contrary, rises on account of the release of the α-tonus.

However, these drug treatments modify certain haemodynamic parameters in a sense which, at a fundamental level, counteracts their beneficial effects for angina pectoris patients in particular, and heart patients in general.

If the antiadrenergic aspect of the β-blockers is considered, it becomes clear that only the tachycardia and the increase in the force and rate of the contraction of the heart are likely to be neutralized, the arterial hypertension resulting from a stimulation of the α-receptors on which β-antagonists have no action.

Now, even though the cardiovascular disturbances brought about by the stimulation of the β-receptors are the most harmful to angina patients, it remains nonetheless true that the arterial hypertension also plays a not insignificant role.

Moreover, the blocking of the β-receptors involves a risk, depriving the patient suffering from cardiac insufficiency of a compensatory mechanism which he normally brings into play to limit his circulatory insufficiency.

This reflex mechanism, the main component of which makes use of the pathway of the β-adrenergic system results, in particular, in an increase in the force and rate of the contraction of the heart. In consequence, if this system is blocked, the patient suffering from cardiac insufficiency experiences an aggravation of his heart failure. Hence, it is logical to consider that the use of a β-blocker whose action is pure and complete, will always involve a cardiac risk.

Hence, it appears desirable not to look for complete α or β-antagonist properties, in view of the clinical side effects they may entail. It seems more reasonable to aim to dampen rather than suppress the cardiovascular disturbances which characterize the hyperstimulation of the adrenergic system as a whole.

The compounds of the invention fulfil this objective since they exhibit incomplete antiadrenergic properties of the α and β types. They can hence be considered, not as β-blockers but as adreno-decelerators, i.e. partial antagonists of the α and β adrenergic reactions, potentially devoid of the disadvantages listed above for β-blockers.

Furthermore, the calcium inhibitory component demonstrated in the compounds of the invention will provide an exceptional complement to the pharmacological spectrum of their cardiovascular action.

In fact, it is known, that the transport of calcium ions is one of the main components of the action potential in heart cells and that, in consequence, this transport plays a fundamental role in electrical conduction as well as in possible disorders (arrhythmia). Furthermore, it is known that calcium ions are implicated in the excitation-contraction coupling which controls the degree of vasoconstriction in smooth muscle and, in the same circumstances, plays a critical role in attacks of angina pectoris.

The compounds which are calcium antagonists act at the level of the cell membrane by selectively preventing calcium from intervening in the process of contraction within the arterial cell.

Now, it is becoming increasingly clear at the present time that the clinical results obtained with the combination of calcium inhibitors and β-adrenergic inhibitors are better than when each inhibitor is used on its own (J.A.M.A. 1982, 247, pages 1911–1917).

Moreover, it seems that at present a β-blocker exerting in addition an appreciable inhibitory action at the level of calcium transport does not exist.

From this point of view, the compounds of the invention exhibiting both an anti-calcium component and an α- and β-antiadrenergic component will be of fundamental value since they are likely to have more extensive therapeutic applications than a β-blocker on its own or a calcium inhibitor on its own. As examples, mention should be made of:

2-isopropyl 8-methyl 1-{4-[3-(N-methyl N-3,5-dimethoxy-β-phenethyl amino)propoxy]benzenesulfonyl-}indolizine (Ex. 76).

2-isopropyl 8-methyl 1-{4-[3-(N-methyl N-3,4-dimethoxy-β-phenethyl amino)propoxy]benzenesulfony}indolizine (Ex. 15).

1-{4-[3-(di-n-butylamino)propoxy]benzenesulfonyl} 2-isopropyl 8-methyl indolizine (Ex. 75)

2-isopropoyl 8-methyl 1-{4-[3-(6,7-dimethoxy 1,2,3,4-tetrahydro isoquinolin-2-yl) propoxy]benzenesulfonyl}indolizine (Ex.2).

2-isopropyl 5-methyl 1-{4-[3-(N-methyl N-3,4-dimethoxy-β-phenethyl amino)propoxy]benzenesulfonyl-}indolizine (Ex. 79).

2-{4-[3-(N-methyl N-3,4-dimethoxy-β-phenethylamino)propoxy]benzenesulfonyl} 5-chloro 3-isopropyl 1-methyl indole (Ex. 59).

However, the major value of these compounds will reside in the fact that, owing to their anti-calcium component, it will be possible to use them in the treatment of angina at rest, a syndrome induced by the appearance of a spasm in the coronary arteries which is combatted at present by compounds such as diltiazem, verapamil or nifedipine.

Moreover, the compounds of the invention have also been shown to be capable of causing a significant increase in coronary output.

The results of pharmacological tests performed for the purpose of determining the cardiovascular properties of the compounds of the invention are listed below.

I. CALCIUM INHIBITORY PROPERTIES

The inhibitory properties of calcium transport at membranes exhibited by the compounds of the invention were demonstrated by measurement of their antagonistic action to the contractile response to potassium-induced depolarization on isolated rat aorta. It is well established that the depolarization of a smooth muscle membrane by potassium makes the latter permeable to extracellular calcium and induces muscle contraction.

Consequently, the measurement of inhibition of the contractile response to depolarization by potassium or the measurement of relaxation of the tonic contraction on potassium depolarization can provide an evaluation of the potency of a compound as an inhibitor of the membrane permeability to $Ca^{++}$ ions.

The technique used is the following:

The aorta is removed from male Wistar rats weighing about 300 g and cut into strips approximately 40 mm long and 3 mm wide.

These fragments are placed in a 25 ml isolated organ bath containing modified Krebs-bicarbonate solution (112 mM NaCL; 5 mM KCl; 25 mM $NaHCO_3$; 1 mM $KH_2PO_4$; 1.2 mM $MgSO_4$; 2.5 mM $CaCl_2$; 11.5 mM glucose, made up to 1000 ml with distilled water) maintained at 37° C. and through which a stream of carbon dioxide is passed. The preparation is connected to a force microsensor and the contractile response is recorded after amplification on a recorder.

A tension of 2g is applied to the preparation. This latter is maintained in the modified Krebs-bicarbonate solution for 60 minutes, and then contractions are induced by replacing the Krebsbi-carbonate solution by a Krebs-potassium solution (17 mM NaCl; 100 mM KCl; 25 mM $NaHCO_3$; 1 mM $KH_2PO_4$; 1.2 mM $MgSO_4$; 2.5 mM $CaCl_2$; 11.5 mM glucose; made up to 1000 ml with distilled water). When the contractile response of the preparation has become reproducible, a given amount of the compound of the invention is introduced into the bath. Sixty minutes later a new spasm is induced by potassium depolarization.

The results obtained on the aorta under investigation are then expressed in percent of the maximal contractional effect before incubation with the test substance.

As examples, the following results were obtained, the compounds of formula (1) being in the form of the free base, the hydrochloride, oxalate or fumarate.

A. Benzofuran derivatives

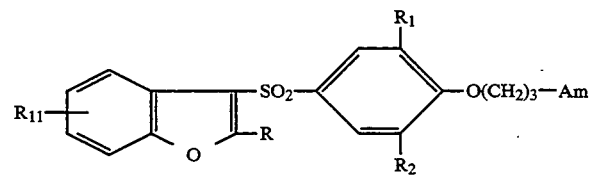

| Compounds | R | $R_1$ et $R_2$ | $R_{11}$ | Am | % maximal contractional effect | |
|---|---|---|---|---|---|---|
| | | | | | $10^{-6}M$ | $10^{-7}M$ |
| Ex. 1 | n-$C_4H_9$ | H | —$NO_2$-5 | —N(CH₃)—(CH₂)₂—C₆H₃(OCH₃)₂ | 45,4 | 70,1 |

-continued

A. Benzofuran derivatives

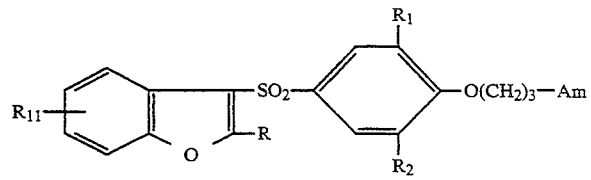

| Compounds | R | $R_1$ et $R_2$ | $R_{11}$ | Am | % maximal contractional effect | |
|---|---|---|---|---|---|---|
| | | | | | $10^{-6}$M | $10^{-7}$M |
| Ex. 2 | n-$C_4H_9$ | H | —$NH_2$-5 | —N(CH$_3$)—(CH$_2$)$_2$—C$_6$H$_3$(OCH$_3$)$_2$ | 24,8 | 71,1 |
| Ex. 4 | n-$C_4H_9$ | H | —$NHSO_2CH_3$-5 | —N(CH$_3$)—(CH$_2$)$_2$—C$_6$H$_3$(OCH$_3$)$_2$ | 49,9 | 92,7 |
| Ex. 8 | n-$C_4H_9$ | H | Br-5 | —N(CH$_3$)—(CH$_2$)$_2$—C$_6$H$_3$(OCH$_3$)$_2$ | 61,5 | 79,4 |
| Ex. 7 | n-$C_4H_9$ | Br | Cl-5 | —N(CH$_3$)—(CH$_2$)$_2$—C$_6$H$_3$(OCH$_3$)$_2$ | 80,3 | 76,8 |

B. - Indole derivatives

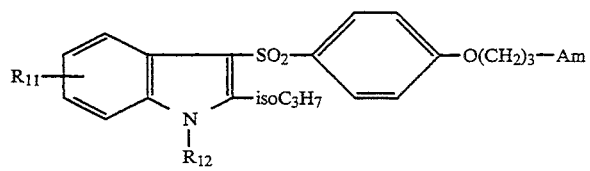

| Compounds | $R_{11}$ | $R_{12}$ | Am | % maximal contractional effect | | | |
|---|---|---|---|---|---|---|---|
| | | | | $10^{-7}$M | $10^{-8}$M | $10^{-9}$M | $10^{-10}$M |
| Ex. 11 | H | —(CH$_2$)$_2$—N(CH$_3$)$_2$ | —N(CH$_3$)—(CH$_2$)$_2$—C$_6$H$_3$(OCH$_3$)$_2$ | 66,7 | 85,9 | — | — |
| Ex. 12 | H | —(CH$_2$)$_2$—N(C$_2$H$_5$)$_2$ | —N(CH$_3$)—(CH$_2$)$_2$—C$_6$H$_3$(OCH$_3$)$_2$ | 74,9 | 84,5 | 90,4 | — |
| Ex. 13 | Cl-5 | CH$_3$ | —N(CH$_3$)—(CH$_2$)$_2$—C$_6$H$_3$(OCH$_3$)$_2$ | 35,5 | 79,2 | — | — |
| Ex. 44 | Cl-5 | CH$_3$ | —N(n-C$_4$H$_9$)$_2$ | 69,6 | 85,7 | — | — |

-continued

B. - Indole derivatives

| | | | | | | | |
|---|---|---|---|---|---|---|---|
| Ex. 45 | $CH_3$-6 | $CH_3$ | $-N(CH_3)-(CH_2)_2$-C$_6$H$_3$(OCH$_3$)$_2$ | 15,7 | 75,2 | 83,2 | — |
| Ex. 46 | $CH_3$-6 | $CH_3$ | $-N(n-C_4H_9)_2$ | 41,7 | 67,2 | 79,5 | — |
| Ex. 47 | Cl-5 | $CH_3$ | $-N(CH_3)$-tetrahydronaphthyl | 75,3 | 88,3 | 91,4 | — |
| Ex. 65 | $CH_3$-4 | $CH_3$ | $-N(CH_3)-(CH_2)_2$-C$_6$H$_3$(OCH$_3$)$_2$ | 14,3 | 29,9 | 76,1 | 83,5 |
| Ex. 66 | $CH_3$-4 | $CH_3$ | $-N(n-C_4H_9)_2$ | 7,1 | 37,1 | 83,1 | — |

3-(S-Ar)-indole structure: $R_{11}$-indole-2-R, 3-S-C$_6$H$_4$-O(CH$_2$)$_3$-Am

| Compounds | $R_{11}$ | R | Am | % maximal contractional effect | | | |
|---|---|---|---|---|---|---|---|
| | | | | $10^{-7}$M | $10^{-8}$M | $10^{-9}$M | $10^{-10}$M |
| Ex. 9 | $OCH_3$-5 | $CH_3$ | $-N(CH_3)-(CH_2)_2$-C$_6$H$_3$(OCH$_3$)$_2$ | 70,4 | 84,4 | 88 | — |

Structure: $R''_{11}$-indole with 3-isoC$_3$H$_7$, 2-SO$_2$-C$_6$H$_4$-O(CH$_2$)$_3$-Am, N-$R_{12}$

| | $R''_{11}$ | $R_{12}$ | Am | $10^{-7}$M | $10^{-8}$M | $10^{-9}$M | $10^{-10}$M |
|---|---|---|---|---|---|---|---|
| Ex. 10 | H | $-(CH_2)_3-N(CH_3)-(CH_2)_2$-C$_6$H$_3$(OCH$_3$,OCH$_3$) | $-N(CH_3)-(CH_2)_2$-C$_6$H$_3$(OCH$_3$)$_2$ | 78,9 | 90,2 | — | — |
| Ex. 55 | $CH_3$ | $CH_3$ | " | 45,8 | 56,4 | 79 | 85,7 |
| Ex. 59 | Cl-5 | $CH_3$ | $-N(CH_3)-(CH_2)_2$-C$_6$H$_3$(OCH$_3$)$_2$ | 41,4 | 55,4 | 68,4 | 81,5 |
| Ex. 61 | $OCH_3$-5 | $CH_3$ | " | 15,7 | 31,2 | 71,4 | 89,5 |
| Ex. 62 | $OCH_3$-5 | H | " | 37,1 | 48,7 | 93,7 | 90,3 |

-continued

B. - Indole derivatives

| Ex. 63 | OCH$_3$-5 | −(CH$_2$)$_3$−N(CH$_3$)−(CH$_2$)$_2$−[3,4-dimethoxyphenyl] | " | 69,7 | 82,8 | 90,8 | — |
|---|---|---|---|---|---|---|---|
| Ex. 64 | OCH$_3$-5 | CH$_3$ | −N(n-C$_4$H$_9$)$_2$ | 69,3 | 72,6 | 93,9 | — |

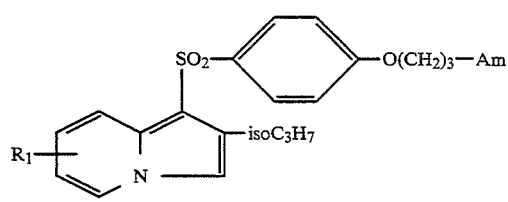

|  |  |  | % maximal contractional effect | | | |
|---|---|---|---|---|---|---|
| Compounds | R"$_{11}$ | R$_{12}$ | Am | $10^{-7}$M | $10^{-8}$M | $10^{-9}$M | $10^{-10}$M |
| Ex. 56 | Cl-5 | CH$_3$ | −N(CH$_3$)−(CH$_2$)$_2$−[3,4-dimethoxyphenyl] | 19,8 | 61,3 | 78,6 | — |
| Ex. 57 | CH$_3$-7 | CH$_3$ | " | 56,9 | 76,4 | 89,9 | — |

C. Indolizine derivatives

|  |  | % maximal contractional effect | | |
|---|---|---|---|---|
| Compounds | R$_{11}$ | Am | $10^{-8}$M | $10^{-9}$M | $10^{-10}$M |
| Ex. 2 | CH$_3$-8 | −N−[6,7-dimethoxy-tetrahydroisoquinoline] | 11,9 | 72,6 | — |
| Ex. 15 | CH$_3$-8 | −N(CH$_3$)−(CH$_2$)$_2$−[3,4-dimethoxyphenyl] | 11,1 | 41,0 | 85,2 |
| Ex. 75 | CH$_3$-8 | −N(n-C$_4$H$_9$)$_2$ | 9,7 | 51,4 | 83,8 |
| Ex. 76 | CH$_3$-8 | −N(CH$_3$)−(CH$_2$)$_2$−[2,5-dimethoxyphenyl] | 12,7 | 41,8 | 64,1 |

C. Indolizine derivatives

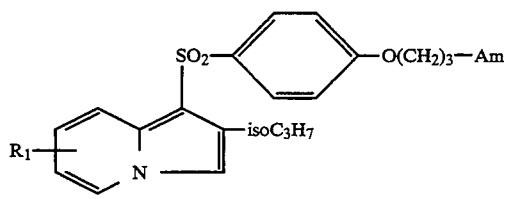

| Compounds | $R_{11}$ | Am | % maximal contractional effect | | |
|---|---|---|---|---|---|
| | | | $10^{-8}M$ | $10^{-9}M$ | $10^{-10}M$ |
| Ex. 79 | $CH_3$-5 | $-N(CH_3)-(CH_2)_2-$C$_6$H$_2$(OCH$_3$)$_3$ | 29,8 | 77,9 | 87,3 |

For the purposes of comparison, the following results were obtained with known compounds (patent FR-A-2.594.438)

| Compounds | $R_{11}$ | Am | % maximal contractional effect | | |
|---|---|---|---|---|---|
| | | | $10^{-8}M$ | $10^{-9}M$ | $10^{-10}M$ |
| B | H | $-N(n-C_4H_9)_2$ | 61 | — | — |
| C | H | $-N(CH_3)-(CH_2)_2-$C$_6$H$_3$(OCH$_3$)$_2$ | 40,1 | 81,7 | — |

D. Pyrazolo[1,5-a]pyridine derivatives

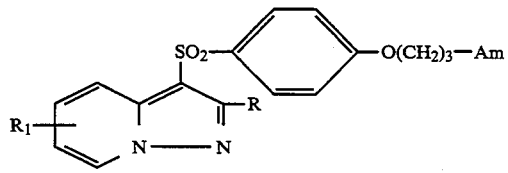

| Compound | R | $R_{11}$ | Am | % maximal contractional effect | | |
|---|---|---|---|---|---|---|
| | | | | $10^{-8}M$ | $10^{-9}M$ | $10^{-10}M$ |
| Ex. 48 | $CH_3$ | $CH_3$-7 | $-N(n-C_4H_9)_2$ | 77,1 | 85,7 | — |
| Ex. 49 | $CH_3$ | $CH_3$-4 | $-N(n-C_4H_9)_2$ | 62,9 | 75,7 | — |
| Ex. 50 | isoC$_3$H$_7$ | $CH_3$-7 | $-N(CH_3)-(CH_2)_2-$C$_6$H$_3$(OCH$_3$)$_2$ | 29,1 | 65,6 | 86,3 |
| Ex. 51 | $CH_3$ | $CH_3$-4 | $-N(CH_3)-$tetrahydronaphthyl | 67,1 | 85 | — |

-continued

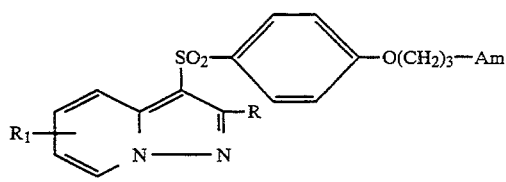

| Compound | R | $R_{11}$ | Am | % maximal contractional effect | | |
|---|---|---|---|---|---|---|
| | | | | $10^{-8}M$ | $10^{-9}M$ | $10^{-10}M$ |
| Ex. 78 | $C_2H_5$ | $CH_3$-4 | —N(CH₃)—(CH₂)₂—C₆H₃(OCH₃)(OCH₃) | 17,5 | 72,9 | 78,6 |
| Ex. 81 | $C_2H_5$ | $CH_3$-6 | " | 78,1 | 85,3 | 91,4 |

E. Benzene Derivatives

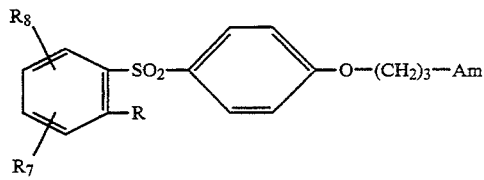

| Compounds | R | $R_7$ | $R_8$ | Am | % maximal contractional effect | | |
|---|---|---|---|---|---|---|---|
| | | | | | $10^{-7}M$ | $10^{-8}M$ | $10^{-9}M$ |
| Ex.6 | $isoC_3H_7$ | $OCH_3$-3 | $OCH_3$-5 | —N(CH₃)—(CH₂)₂—C₆H₃(OCH₃)(OCH₃) | 13,1 | 63,4 | 85,7 |

II. Antiadrenergic Properties

The aim of this test is to determine the capacity of the compounds of the invention to reduce the increase in blood pressure induced by epinephrine (anti-α effect) and the acceleration of the heart rate induced by isoprenaline (anti-β effect) in the dog previously anesthetized with pentobarbital and atropinized.

First, are determined for each dog the dose of epinephrine (between 3 and 10 µg/kg) which causes a reproducible increase in arterial blood pressure of about $133.10^2$ Pa and the dose of isoprenaline (1 to 2 µg/kg) which causes a reproducible increase in the heart rate of about 70 beats/minute. The doses of epinephrine and isoprenaline thus determined are injected alternatively every ten minutes and after the two consecutive reference responses have been obtained, a quantity of the test compound is administered by the intravenous route.

-Anti-α effect

The percentage reduction of the hypertension caused by the test compound in comparison with the reference hypertension previously obtained (about 100 mm Hg) is recorded.

-Anti-β effect

The percentage reduction of the acceleration of the heart rate caused by the test compound compared with the reference tachycardia previously measured (about 70 beats) is recorded.

In both cases, the results of the reduction in arterial pressure and heart rate are expressed as follows:

+ for a reduction <50%
++ for a reduction ≧50%
+++ for an almost complete reduction The following results were recorded:

| A. Benzofuran derivatives | | | |
|---|---|---|---|
| Compounds | Dose (mg/kg) | Anti-α effect | Anti-β effect |
| Ex. 1 | 3,23 | +++ | ++ |
| Ex. 3 | 1,31 | +++ | ++ |
| Ex. 8 | 1,5 | +++ | +++ |

| B. Indole derivatives | | | |
|---|---|---|---|
| Compounds | Dose (mg/kg) | Anti-α effect | Anti-β effect |
| Ex. 10 | 4,9 | +++ | +++ |
| Ex. 11 | 1,6 | ++ | + |
| Ex. 47 | 6,6 | ++ | ++ |
| Ex. 13 | 0,6 | +++ | ++ |
| Ex. 14 | 0,12 | +++ | + |
| Ex. 65 | 0,1 | +++ | +++ |
| Ex. 44 | 1,2 | ++ | ++ |
| Ex. 66 | 0,05 | +++ | +++ |
| Ex. 55 | 0,07 | +++ | +++ |
| Ex. 56 | 0,67 | +++ | ++ |
| Ex. 61 | 0,035 | +++ | ++ |
| Ex. 62 | 1 | +++ | ++ |

-continued

B. Indole derivatives

| Compounds | Dose (mg/kg) | Anti-α effect | Anti-β effect |
|---|---|---|---|
| Ex. 64 | 0,5 | +++ | ++ |

C. Indolizine derivatives

| Compounds | Dose (mg/kg) | Anti-α effect | Anti-β effect |
|---|---|---|---|
| Ex. 75 | 0,02 | ++ | ++ |
| Ex. 2 | 0,065 | +++ | +++ |
| Ex. 76 | 0,013 | +++ | +++ |
| Ex. 79 | 0,07 | +++ | ++ |
| Ex. 15 | 0,013 | ++ | + |

For the purposes of comparison, the following results were obtained with the following known composed mentioned below:

| Compounds | Dose (mg/kg) | Anti-α effect | Anti-β effect |
|---|---|---|---|
| B | 0,5 | ++ | ++ |
| C | 0,1 | +++ | +++ |

D. Pyrazolo[1,5-a]pyridine derivatives

| Compounds | Dose (mg/kg) | Anti-α effect | Anti-β effect |
|---|---|---|---|
| Ex. 49 | 0,28 | + | + |
| Ex. 50 | 0,13 | +++ | +++ |

III—Toxicity

The toxicity of the compounds of the invention is shown to be compatible with their use in therapy.

The therapeutic compositions according to the invention can be made available in any form suitable for administration in human or veterinary medicine. As far as the unit of administration is concerned, it may take the form, for example, of a tablet, a sugar-coated pill, a capsule, a powder, a suspension or a syrup in case or oral administration, a suppository for rectal administration and a solution or suspension for parenteral administration.

The therapeutic compositions of the invention will contain, per administration unit, for example from 50 to 500 mg by weight of active ingredient for oral administration, from 50 to 200 mg of active ingredient for rectal administration and from 50 to 150 mg of active ingredient for parenteral administration.

Depending on the route of administration selected, the therapeutic or veterinary compositions of the invention will be prepared by combining at least one of the compounds of formula (1) or a non-toxic addition salt of this compound with a suitable excipient, this latter being constituted, for example, by at least one ingredient selected from the following substances: lactose, starches, talc, magnesium stearate, polyvinylpyrrolidone, alginic acid, colloidal silica, distilled water, benzyl alcohol or sweetening agents.

The following non-limiting examples illustrate the invention:

EXAMPLE 1

Preparation of 2-n-butyl 3-{4-[3-(N-methyl N-3,4-dimethoxy-β-phenethyl amino)propoxy]benzenesulfonyl} 5-nitro benzofuran hydrochloride (SR 33633 A)

a) 2-n-Butyl 3-(4-hydroxy benzenesulfonyl) 5-nitro benzofuran

A mixture of 2.6 g (0.011 mole) of p-methoxybenzenesulfonyl chloride, 1.6 g of aluminium chloride and 40 ml of dichloroethane is stirred for 5 min at 20° C. It is cooled to 0° C. and 2.5 g (0.011 mole) of 2-n-butyl 5-nitro benzofuran in 3 ml of dichloroethane are added. The mixture is allowed to rise to room temperature during 1 h, 1.4 g of aluminium chloride are added and the mixture is stirred for a further 2 hours. After a further addition of 4.2 g of aluminium chloride, the mixture is refluxed for 20 min. It is poured into a mixture of ethylether/water/ice and washed 3 times with water. It is treated with 300 ml of a 2% sodium hydroxide solution, then the brown aqueous phase is washed with ethylether. This aqueous phase is treated with a concentrated solution of hydrochloric acid, then the phenolic derivative is extracted with ethylether. The organic phase is shaken in the presence of sodium sulfate and animal charcoal, filtered and concentrated.

In this manner, 2.8 g of 2-n-butyl 3-(4-hydroxybenzenesulfonyl) 5-nitro benzofuran are obtained in a yield of 68%. U.V. Spectrum (methanol): λ max: 246 cm$^{-1}$ 204 cm$^{-1}$.

b) 2-n-Butyl 3-[4-(3-bromopropoxy)benzenesulfony] 5-nitro benzofuran

A mixture of 14 mmoles of 2-n-butyl 3-(4-hydroxybenzenesulfonyl) 5-nitro benzofuran and 20 mmoles of potassium carbonate in 30 ml of N,N-dimethylformamide is heated for 1 min at 120° C. 280 mmoles of 1,3-dibromopropane are added and stirring is continued for 15 minutes at this temperature. The mixture is poured into water and extracted with ethylether. The extract is dried over sodium sulfate, filtered and concentrated. It is then purified on a column of silica using an ethyl acetate/n-hexane mixture 4/6.

In this manner, 10.8 mmoles of 2-n-butyl 3-[4-(3-bromopropoxy)benzenesulfonyl] 5-nitro benzofuran are obtained after recrystallization from an ethylether/pentane mixture.

Yield: 77%.

M.p.: 101° C.

c) 2-n-Butyl 3-{4-[3-(N-methyl N-3,4-dimethoxy-β-phenethyl amino)propoxy]benzenesulfony} 5-nitro benzofuran hydrochloride.

A mixture of 8 mmoles of 2-n-butyl 3-[4-(3-bromopropoxy)benzenesulfony] 5-nitro benzofuran, 10 mmoles of potassium carbonate and 8 mmoles of N-methyl 3,4-dimethoxy phenethylamine in 14 ml of N,N-dimethylformamide is stirred for 10 to 12 hours at room temperature. The mixture is poured into water and extracted with an ethyl acetate/dichloromethane mixture 8/2. The extract is concentrated and eluted from a column of silica successively by methanol and acetone to give 4.8 mmoles (yield: 60%) of the required compound in the form of the base. This oil is dissolved in toluene and the solution is treated with hydrochloric acid.

In this manner, 2-n-butyl 3-{4-[3-(N-methyl N-3,4-dimethoxy-β-phenethylamino)propoxy]benzenesulfonyl} 5-nitro benzofuran hydrochloride is obtained.

M.p.: 162.9° C. (methyl ethyl ketone)

EXAMPLE 2

Preparation of 2-isopropyl 8-methyl 1-{4-[3-(6,7-dimethoxy 1,2,3,4-tetrahydro N-isoquinolin-2-yl)propoxy]benzenesulfonyl}indolizine hydrogen oxalate (SR 33873 A)

a) 4-methoxy benzenesulfonyl 2-methyl 3-methyl pyridine

A mixture of 0.050 mole of 2-chloromethyl 3-methyl pyridine hydrochloride, 0.050 mole of sodium 4-methoxy benzenesulfinate and 0.070 mole of sodium bicarbonate in 20 ml of toluene containing 0.8 g of methyltrioctylammonium chloride is stirred at 80° C. for 2.5 hours. It is cooled, poured into 100 ml of water and extracted 3 times with 125 ml of ethyl acetate to give 17 g of a brownish paste which is purified on a column of silica (solvent: dichloromethane/ethyl acetate 5/1).

In this manner, 4-methoxy benzenesulfonyl 2-methyl 3-methyl pyridine is obtained as a white solid in a yield of 85.2%.

Purity: 98.9%
M.p.: 84°–85° C.

b) 2-isopropyl 8-methyl 1-(4-methoxy benzenesulfonyl)indolizine

A mixture of 11.6 g (0.0495 mole) of 4-methoxy benzenesulfonyl 2-methyl 3-methyl pyridine, 7.2 g (0.051 mole) of potassium carbonate and 21.2 g (0.128 mole) of bromomethyl isopropyl ketone is stirred at reflux for 48 hours. The solvent and the excess bromoketone are removed in a vacuum and the residue is taken up in water. It is extracted with dichloromethane, the product is isolated and purified on a column of silica (eluant:dichloromethane).

In this manner, 10.8 g of 2-isopropyl 8-methyl 1-(4-methoxybenzenesulfonyl)indolizine are obtained in the form of a white solid.

Yield: 74%
M.p.: 103° C. (ethyl acetate/n-hexane)
Purity: 99% c) 2-isopropyl 8-methyl 1-(4-hydroxy benzenesulfonyl)indolizine 15 g (0.024 mole) of 50% sodium hydride in oil is suspended in 20 ml of N,N-dimethylformamide. 0.012 mole of 2-thioethanol is added to it and the mixture is stirred for 15 minutes at room temperature. 2 g (0.00582 mole) of 2-isopropyl 8-methyl 1-(4-methoxy benzenesulfonyl)indolizine are then introduced in small portions and the mixture is heated at 130° C. After 45 minutes, thin layer chromatography indicates that the starting methoxylated product has been completely converted. The mixture is cooled, poured into water and the oil obtained is extracted with hexane. The aqueous layer is acidified and extracted with ethyl acetate. Purification is performed on a column of silica by eluting with a dichloromethane/ethyl acetate mixture 80/20.

In this manner, 2-isopropyl 8-methyl 1-(4-hydroxybenzenesulfonyl)indolizine is obtained in the form of a white solid.

Yield: 100%
M.p.: 191°–193° C.
Purity: 98.72% d) 2-isopropyl 8-methyl 1-{4-[3-(6,7-dimethoxy 1,2,3,4-tetrahydro-N-isoquinolin-2-yl)propoxy]benzenesulfonyl}indolizine hydrogen oxalate A mixture of 2 g (6 mmoles) of 2-isopropyl 8-methyl 1-(4-hydroxy benzenesulfonyl)indolizine in 10 ml of N,N-dimethylformamide is heated at 50° C. for 0.5 h. 1.6 g (6 mmoles) of 2-(3-chloropropyl) 6,7-dimethoxy 1,2,3,4-tetrahydroisoquinoline are added and the mixture is heated with stirring at 80°–90° C. for 3 hours. The mixture is cooled, poured into water and extracted with dichloromethane. The oil thus obtained is then purified by chromatography on silica (eluant:ethyl acetate/methanol 9/1) which gives 2.7 g of an oil composed of the required compound in the basic form. This oil solidifies on being left to stand. This base is then dissolved in methanol and one equivalent of oxalic acid is added which leads to the precipitation of an oxalate after about 10 minutes. It is redissolved by heating and left to crystallize.

In this manner, 3.35 g of 2-isopropyl 8-methyl 1-{4-[3-(6,7-dimethoxy 1,2,3,4-tetrahydro N-isoquinolin-2-yl)propoxy]benzenesulfonyl}indolizine hydrogen oxalate are obtained in the form of a white solid.

Yield: 85.5% M.p.: 199°–200° C.
Purity: 98.2%

EXAMPLE 3

Preparation of 5-amino 3-{4-[3-(N-methyl N-3,4-dimethoxy-β-phenethyl amino)propoxy]benzenesulfonyl} 2-n-butyl benzofuran dihydrochloride (SR 33668 A)

A solution of 2-n-butyl 3-{4-[3-(N-methyl N-3,4,-dimethoxy-β-phenethylamino)propoxy]benzenesulfonyl} 5-nitro benzofuran in the form of the base in 80 ml of absolute ethanol is stirred in the presence of 0.2 g of platinum oxide under an atmosphere of hydrogen for 2 hours. It is filtered and evaporated to dryness. The residue is taken up in ethyl acetate and purified on a column of silica neutralized by diethylamine by eluting with ethyl acetate containing 10% of methanol, which gives 4.15 g (yield: 80%) of the required compound as the free base. 1.5 g of this base dissolved in dry ethylether is then treated with hydrogen chloride in ether. The product is filtered off and recrystallized twice from an acetone/methanol mixture.

In this manner, 0.55 g of 5-amino 3-{4-[3-(N-methyl N-3,4-dimethoxy-β-phenethylamino)propoxy]benzenesulfonyl} 2-n-butyl benzofuran dihydrochloride in a yield of 33% is obtained. M.p.: 163° C.

EXAMPLE 4

Preparation of 3-{4-[3-(N-methyl N-3,4-dimethoxy-β-phenethylamino)propoxy]benzenesulfonyl} 2-n-butyl 5-methane sulfonamido benzofuran hydrogen oxalate (SR 33669 A)

A solution of 5-amino 3-{4-[3-(N-methyl N-3,4-dimethoxy-β-phenethylamino)propoxy]benzenesulfonyl} 2-n-butyl in the form of the free base and triethylamine in 25 ml of dry dichloroethane is treated dropwise with 0.84 g of methane sulfonyl chloride in 10 ml of dichloroethane. Stirring is continued for 3 hours, the mixture is washed with water and evaporated to dryness. The residue is purified on a column of silica, treated with diethylamine by eluting with ethyl acetate containing 2.5% methanol. A solution of the required compound in the form of the free base is then treated with an oxalic acid solution.

In this manner, 0.5 g of 3-{4-[3-(N-methyl N-3,4-dimethoxy-β-phenethylamino)propoxy]benzenesulfonyl} 2-n-butyl 5-methane sulfonamido benzofuran hydrogen oxalate is obtained.

Yield: 15%
M.p.: about 83° C.

EXAMPLE 5

Preparation of 1-{4-[3-(N-methyl N-3,4-dimethoxy-β-phenethylamino)propoxy]benzenesulfonyl} 2-isopropyl 6-ethoxy indolizine hydrogen oxalate a) 2-acetoxymethyl 5-ethoxy pyridine 18.3 g of 2-methyl 5-ethoxy pyridine-N-oxide are heated at reflux in 125 ml of acetic anhydride for 3 hours. The acetic acid and acetic anhydride are removed in a vacuum and the oily residue is distilled in a vacuum.

In this manner, 2-acetoxymethyl 5-ethoxy pyridine is obtained in a yield of 75.9%.

B.p.: 105°–110° C. (7.5×10$^{-2}$ Torr)

b) 2-chloromethyl 5-ethoxy pyridine hydrochloride 20 g (0.102 mole) of 2-acetoxymethyl 5-ethoxy pyridine in 85 ml of ethanol and 195 ml of N sodium hydroxide are refluxed for 1.5 hours. Ethanol is evaporated in a vacuum, the aqueous phase is acidified and extracted with ethyl acetate. The extract is washed with water and 15 g of carbinol are thus isolated practically pure. This carbinol is taken up in 60 ml of chloroform, 0.12 mole of thionyl chloride is added and the mixture is refluxed for 2 hours. It is evaporated to dryness in a vacuum, the tacky residue obtained is taken up in 100 ml of acetone and stirred at room temperature for 10 to 12 hours to form a solid product. The product is diluted with 100 ml of anhydrous ethylether and filtered off.

In this manner, 19 g of 2-chloromethyl 5-ethoxy pyridine hydrochloride are obtained in the form of a brownish white solid.

Yield: 89.5%

M.p.: 75° C. (isopropanol/acetone/ethylether).

c) 4-benzyloxy benzensulfonyl 2-methyl 5-ethoxypyridine 2.6 g (10 mmoles) of 2-chloromethyl 5-ethoxypyridine hydrochloride, 13 mmoles of sodium bicarbonate and 10 mmoles of sodium 4-benzyloxy benzenesulfinate are stirred in the absence of solvent. 20 drops of methyltrioctylammonium chloride are added, the mixture is heated on an oil bath at 80° C. and 10 ml of toluene are added to fluidize the reaction mixture so that it can be stirred. After 2 h at this temperature, it is poured into water and extracted with ethyl acetate. 4.4 g of a beige solid are thus obtained which is purified by chromatography on silica using a dichloroethane/ethyl acetate mixture 90/10.

In this manner, 2.6 g of 4-benzyloxy benzenesulfonyl 2-methyl 5-ethoxy pyridine are obtained.

M.p.: 133°–134° C. (ethyl acetate/n-hexane).

d) 1-(4-benzyloxy benzenesulfonyl) 2-isopropyl 6-ethoxy indolizine 16.95 g (0.044 mole) of 4-benzyloxy benzenesulfonyl 2-methyl 5-ethoxy pyridine, 22 g (0.133 mole) of bromomethyl isopropyl ketone and 7.75 g (0.055 mole) of potassium carbonate in 150 ml of methyl ethyl ketone are heated at reflux for 24 hours. A further 11 g (1.5 equivalents) of bromomethyl isopropoyl ketone and 8 g of potassium carbonate are then added and reflux is continued for an additional 24 hours. The solvent is then evaporated, the residue is taken up in water and extracted with dichloromethane. The extracts are washed with water and the organic phase is isolated. The excess bromoketone is removed in a vacuum and 26 g of a brownish oil are thus obtained. It is triturated with anhydrous ether for several hours and the solid formed is filtered off and washed with ethylether.

In this manner, 1-(4-benzyloxy benzenesulfonyl) 2-isopropyl 6-ethoxy indolizine is obtained which is recrystallized from an acetone/water mixture 3/1.

Yield: 69.9%

M.p.: 153° C.

e) 1-(4-hydroxy benzenesulfonyl) 2-isopropyl 6-ethoxy indolizine 1.3 g of 1-(4-benzyloxy benzenesulfonyl) 2-isopropyl 6-ethoxy indolizine, 0.9 g of 10% palladium on charcoal and 1.5 g of ammonium formate are boiled in 50 ml of methanol for 2 hours. The mixture is filtered and the filtrate is evaporated to dryness to give 0.8 g of a white solid which is purified on a column of silica (eluant:dichloromethane), then recrystallized from a methanol/water mixture.

In this manner, 0.6 g of 1-(4-hydroxy benzenesulfonyl) 2-isopropyl 6-ethoxy indolizine is obtained in a yield of 60%.

M.p.: 220°–221° C.

Purity: 100% f) 1-{4-[3-(N-methyl N-3 4-dimethoxy-$\beta$-phenethyl amino)propoxy]benzenesulfonyl} 2-isopropyl 6-ethoxy indolizine hydrogen oxalate (SR 33890 A)

The compound was obtained in accordance with the method described in Example 2.

M.p.: 146° C. (ethyl acetate/methanol/ethylether).

EXAMPLE 6

Preparation of 4-[-3(N-methyl N-3,4-dimethoxy-$\beta$-phenethylamino)propox]phenyl (2-isopropyl 3,5-dimethoxy phenyl) sulfone oxalate (SR 33771 A)

a) 2-(4-hydroxy benzenesulfonyl) 1-isopropyl 3,4-dimethoxy benzene

A mixture of 2 g (0.011 mole) of 1-isopropyl 3,4-dimethoxy benzene, 3.4 g (0.011 mole) of sodium 4-benzyloxy benzenesulfonate, 45 ml of anhydrous methanesulfonic acid and 4.5 g of phosphoric anhydride is stirred at 50° C. for 5 hours. It is poured into an ice/water mixture, the product is filtered off and washed on the filter with water. The still moist solid is taken up in 20 ml of ethanol and 5 ml of a 30% sodium hydroxide solution. It is heated at 60° C. for about 2 h until dissolution is complete, the solution is diluted with water, filtered and acidified with acetic acid. The product is filtered off and washed on the filter with water. It is then purified by chromatography on a column of silica using a dichloroethane/ethyl acetate mixture 95/5.

In this manner, 1.5 g of 2-(4-hydroxy benzenesulfonyl) 1-isopropyl 3,5-dimethoxy benzene are obtained.

Yield: 40% b) 4-[3-(N-methyl N-3,4-dimethoxy-$\beta$-phenethylamino)propoxy]phenyl (2-isopropyl 3,5-dimethoxyphenyl)sulfone oxalate This compound was obtained in accordance with the method described in Example 2.

M.p.: 105° C. (ethyl acetate/isopropanol).

The following compounds have been prepared, using the procedures previously described:

5-chloro 2-n-butyl 3-{4-[3-(N-methyl N-3,4-dimethoxy-$\beta$-phenethylamino)propoxy] 3,5-dibromobenzenesulfonyl}benzofuran hydrogen oxalate (SR 33851 A) (Example 7)- M.p.: 114° C. (ethanol)

5-bromo 2-n-butyl 3-{4[3-(N-methyl N-3,4-dimethoxy-$\beta$-phenethyl amino)propoxy]benzenesulfonyl}benzofuran hydrogen oxalate (SR 33844 A) (Example 8). M.p.: 114° C.

3-{4-[3-(N-methyl N-3,4-dimethoxy-$\beta$-phenethyl amino)propoxy]phenylthio} 5-methoxy 2-methyl indole hydrogen oxalate (SR 33875 A) (Example 9). M.p.: 162° C. (ethanol/methanol 1/1).

2-{4-[3-(N-methyl N-3,4-dimethoxy-$\beta$-phenethyl amino)propoxy]benzenesulfonyl} 1-[3-(N-methyl N-3,4-dimethoxy-$\beta$-phenethyl amino)propyl] 3-isopropyl indole dioxalate (SR 33806 A) (Example 10). M.p.: about 115° C. (isopropanol/ethyl acetate).

3-{4-[3-(N-methyl N-3,4-dimethoxy-$\beta$-phenethyl amino)propoxy]benzenesulfonyl} 1-dimethylaminoethyl 2-isopropyl indole dioxalate (SR 33788 A) (Example 11). M.p.: 114° C. (sinters).

3-{4-[3-(N-methyl N-3,4-dimethoxy-β-phenethyl amino)propoxy]benzenesulfonyl} 1-diethylaminoethyl 2-isopropyl indole dioxalate (SR 33782 A) (Example 12). M.p.: sinters from 115° C. (isopropanol/ethyl acetate).

3-{4-[3-(N-methyl N-3,4-dimethoxy-β-phenethyl amino)propoxy]benzenesulfonyl} 5-chloro 2-isopropyl 1-methylindole (SR 33867) (Example 13) M.p.: 92.7° C.

2-isopropyl 3-methyl 1-{4-[3-(N-3,4-dimethoxy-β-phenethyl amino)propoxy]benzenesulfonyl}indolizine hydrogen oxalate (SR 33762 A) (Example 14) M.p.: 157°–158° C.

2-isopropyl 8-methyl 1-{4-[3-(N-methyl N-3,4-dimethoxy-β-phenethylamino)propoxy]benzenesulfonyl}indolizine hydrogen oxalate (SR 33871 A) (Example 15) M,p,: 161° C.

1-[4-(4-methylbenzenesulfonyl)phenyloxy] 3-(4-methyl piperazin-1-yl) 2-propanol dihydrochloride (LB 31808) (Example 16). M. p.: 206°–208° C.

4-(3-dimethylamino propyloxy) 4'methyl diphenylsulfone hydrogen oxalate (LB 31804) (Example 17) M.p.: 131°–133° C.

4-(3-di-n-propylamino propyloxy) 4'-methyl diphenylsulfone hydrogen oxalate (LB 31805) (Example 18) M.p.: 90°–92° C.

4-(3-diethylamino propyloxy) 4'-methyl diphenylsulfone hydrogen oxalate (LB 31806) (Example 19) M.p.: 118°–120° C.

4-(3-di-n-butylamino propyloxy) 4'-methyl diphenylsulfone hydrogen oxalate (LB 31770) (Example 20). M.p.: 116°–118° C.

4-(2-dimethylamino ethyloxy) 4'-methyl diphenylsulfone hydrochloride (LB 31771) (Example 21) M.p.: 143°–145° C.

4-(2-diethylamino ethyloxy) 4'-methyl diphenylsulfone hydrochloride (LB 31772) (Example 22). M.p.: 153°–154° C.

3-[4-(4-methoxyphenyl)piperazin-1-yl] 1-[4-(4-methyl benzenesulfonyl)phenyloxy] 2-propanol (LB 31853) (Example 23). M.p.: 124°–127° C.

3-[4-(4-chlorophenyl)piperazin-1-yl] 1-[4-(4-methyl benzenesulfonyl)phenyloxy] 2-propanol hydrochloride (LB 31902) (Example 24). M.p.: 228°–229° C.

3-[4-(2-chlorophenyl)piperazin-1-yl] 1-[4-(4-methyl benzenesulfonyl)phenyloxy] 2-propanol hydrochloride (LB 31903) (Example 25). M.p.: 226°–227° C.

3-[4-(2-methoxyphenyl)piperazin-1-yl ] 1-[4-(4-methyl benzenesulfonyl)phenyloxy] 2-propanol dihydrochloride (LB 31916) (Example 26) M.p.: 198°–200° C.

1-[2,3-dichloro 4-(4-methyl benzenesulfonyl)phenyloxy] 3-[4-(2-methoxyphenyl)piperazin-1-yl] 2-propanol (LB 32776) (Example 27). M.p.: 159°–160° C.

1-[2,3-dichloro 4-(4-methyl benzenesulfonyl)phenyloxy] 3-N-tert-butyl amino 2-propanol hydrochloride (LB 32803) (Example 28). M.p.: 221°–223° C.

1-[4-(2-chlorophenyl)piperazin-1-yl] 3-[2,3-dichloro 4-(4-methyl benzenesulfonyl)phenyloxy] 2-propanol (LB 32804) (Example 29). M.p.: 141°–145° C.

1-[2,3-dichloro 4-(4-methyl benzenesulfonyl)phenyloxy] 3-N-isopropylamino 2-propanol hydrochloride (LB 32856) (Example 30). M.p.: 212°–213° C.

1-[2,3-dichloro 4-(4-methoxy benzenesulfonyl)phenyloxy] 3-[4-(2-methylphenyl)piperazin-1-yl] 2-propanol (LB 32956) (Example 31). M.p.: 147°–148° C.

1-[2,3-dichloro 4-(4-methyl benzenesulfonyl)phenyloxy] 3-[4-(2-methylphenyl)piperazin-1-yl] 2-propanol (LB 32957) (Example 32). M.p.: 144–°145° C.

1-[2,3-dichloro 6-(4-methoxy benzenesulfonyl)phenyloxy] 3-[4-(2-methoxy phenyl)piperazin-1-yl] 2-propanol hydrochloride (LB 32986) (Example 33). M.p.: 190°–192.5° C.

1-[4-(2-chlorophenyl)piperazin-1-yl] 3-[2,3-dichloro 4-(4-methoxy benzenesulfonyl)phenyloxy] 2-propanol (LB 32988) (Example 34). M.p.: 155°–157° C.

1-[2,3-dichloro 4-(4-methoxy benzenesulfonyl)phenyloxy] 3-[2-(3,4-dimethoxyphenyl)ethylamino] 2-propanol hydrochloride (LB 32989) (Example 35). M.p.: 162°–170° C.

1-[2,3-dichloro 6-(4-methoxy benzenesulfonyl)phenyloxy] 3-[4-(2-methylphenyl)piperazin-1-yl] 2-propanol hydrochloride (LB 33007) (Example 36). M.p.: 135°–137° C.

1-[2,3-dichloro 6-(4-methoxy benzenesulfonyl)phenyloxy] 3-[4-(2-chlorophenyl)piperazin-1-yl] 2-propanol hydrochloride (LB 32008) (Example 37). M.p.: 140°–142° C.

1-[2,3-dichloro 6-(4-methyl benzenesulfonyl)phenyloxy] 3-[4-(2-methoxyphenyl)piperazin-1-yl] 2-propanol hydrogen oxalate (LB 33015) (Example 38). M.p.: 181°–183° C.

1-[2,3-dichloro 4-(4-methyl benzenesulfonyl)phenyloxy] 3-[4-(2-methylphenyl)piperazin-1-yl] 2-propanol hydrochloride (LB 32016) (Example 39). M.p.: 178°–180° C.

1-[2,5-dichloro 4-(4-methyl benzenesulfonyl)phenyloxy] 3-N-isopropylamino 2-propanol hydrochloride (LB 33097) (Example 40). M.p.: 209°–210° C.

1-[2,6-dichloro 4-(4-methyl benzenesulfonyl)phenyloxy] 3-[4-(2-methoxyphenyl)piperazin-1-yl] 2-propanol hydrochloride (LB 33096) (Example 41). M.p.: 193.5°–194° C.

1-[2-chloro 4-(4-methyl benzenesulfonyl)phenyloxy] 3-N-isopropylamino 2-propanol hydrochloride (LB 33098) (Example 42) M.p.: 205°–206° C.

2-N-cyclohexylamino 3-[2,3-dichloro 6-(4-methoxy benzenesulfonyl)phenyloxy] 2-propanol hydrogen oxalate (LB 33094) (Example 43). M.p.: 209°–211° C.

1-methyl 2-isopropyl 3-{4-[3-(di-n-butylamino)propoxy]benzenesulfonyl} 5-chloro indole hydrogen oxalate (SR 33879 A) (Example 44). M.p.: 155° C. (ethanol).

1-methyl 2-isopropyl 3-{4-[3-(N-methyl N-3,4-dimethoxy-β-phenethylamino)propoxy]benzenesulfony} 6-methyl indole hydrogen oxalate (SR 33884 A) (Example 45). M.p.: 153° C. (isopropanol).

1-methyl 2-isopropyl 3-{4-[3-(di-n-butylamino)propoxy]benzenesulfonyl} 6-methyl indole hydrogen oxalate (Example 46) (SR 33930 A) M.p.: about 80° C. (sinters) (isopropanol).

1-methyl 2-isopropyl 3-{4-[3-(N-methyl N-1,2,3,4-tetrahydro naphth-1-yl amino)propoxy]benzenesulfonyl} 5-chloro indole hydrogen oxalate (Example 47) (SR 33925 A) M.p.: about 105° C. (ethyl acetate/isopropanol).

3-{4-[3-(di-n-butylamino)propoxy]benzenesulfonyl} 2,7 dimethyl pyrazolo[1,5-]pyridine hydrogen oxalate (SR 33889 A) (Example 48). M.p.: 129° C. (isopropanol).

3-{4-[3-(di-n-butylamino)propoxy]benzenesulfonyl} 2,4-dimethyl pyrazolo[1,5-a]pyridine hydrogen oxalate (SR 33895 A) (Example 49). M.p.: 148° C. (ethanol).

3-{4-[3-(N-methyl N-3,4-dimethoxy-β-phenethylamino)propoxy]benzenesulfonyl} 2-isopropyl 7-methyl pyrazolo[1,5-a]pyridine hydrogen oxalate (SR 33897 A) (Example 50). M.p.: 164° C. (ethanol).

3-{4-[3-(N-methyl N-1,2,3,4-tetrahydro napth-1-yl amino)propoxy]benzenesulfonyl} 2,4-dimethyl pyrazolo[1,5-a]pyridine hydrogen oxalate (SR 33902 A) (Example 51). M.p.: 121.9° C. (ethanol/diethylether).

3-{4-[3-(di-n-butylamino) propoxy]benzenesulfonyl} 2-isopropyl 7-methyl pyrazolo[1,5-a]pyridine hydrogen oxalate (Example 52). 1-{4-[3-(di-n-butylamino)propoxy]benzenesulfonyl} 2-isopropyl 6-ethoxy indolizine (Example 53) (SR 33904). M.p.: 74.5° C. (ethanol/water 2/1).

6-benzyloxy 2-isopropyl 1-{4-[3-(di-n-butylamino)propoxy]benzenesulfonyl}indolizine hydrochloride (SR 33655 A) (Example 54). M.p.: 168°-169° C. (ethyl acetate/methanol).

2-{4-[3-(N-methyl N-3,4-dimethoxy-β-phenethylamino)propoxy]benzenesulfonyl} 3-isopropyl 1,7-dimethyl indole hydrogen oxalate (SR 33931 A) (Example 55) M.p.: 186° C. (methanol)

(5-chloro 3-isopropyl 1-methylindo-2yl)4-[3-(N-methyl N-3,4-dimethoxy-β-phenethylamino)propoxy]phenyl sulfoxide hydrogen oxalate (SR 33933 A) (Example 56). M.p.: about 85° C. (isopropanol)

(3-isopropyl 1,7-dimethylindol-2-yl)4-[3-(N-methyl N-3,4-dimethoxy-β-phenethylamino)propoxy]phenyl sulfoxide hydrogen oxalate (SR 33934 A) (Example 57). M.p.: 168° C. (ethanol).

2-{4-[3-(N-methyl N-3,4-dimethoxy-β-phenethylamino)propoxy]benzenesulfonyl} 5-chloro 3-isopropyl 1-methyl indole a) base (SR 33941) (Example 58). M.p.: begins to sinter at 50° C.

b) Hydrogen oxalate (SR 33941 A) (Example 59) M.p.: 178.5° C. (ethanol)

c) Hydrochloride (SR 33941 B) (Example 60) M.p.: 134° C. (ethyl acetate/ethylether)

2-{4-[3-(N-methyl N-3,4-dimethoxy-β-phenethylamino)propoxy]benzenesulfonyl} 3-isopropyl 5-methoxy 1-methyl indole hydrogen fumarate (SR 33949 A) (Example 61) M.p.: 150.3° C. (ethanol)

2-{4-[3-(N-methyl N-3,4-dimethoxy-β-phenethylamino)propoxy]benzenesulfonyl} 3-isopropyl 5-methoxy indole hydrogen oxalate (SR 33958 A) (Example 62) M.p.: about 98° C. (ethylether)

2-{4-[3-(N-methyl N-3,4-dimethoxy-β-phenethylamino)propoxy]benzenesulfonyl} 1-[3-(N-methyl N-3,4-dimethoxy-β-phenethylamino)propyl] 3-isopropyl 5-methoxy indole oxalate (SR 33959 A) (Example 63) M.p.: about 96° C. (ethylether)

2-{4-[3-(di-n-butylamino)propoxy]benzenesulfonyl} 3-isopropyl 5-methoxy 1-methyl indole hydrogen oxalate (SR 33965 A) (Example 64) M.p.: 93° C. (isopropanol/ethylether)

3-{4-[3-(N-methyl N-3,4-dimethoxy-β-phenethylamino)propoxy]benzenesulfonyl} 2-isopropyl 1,4-dimethyl indole hydrogen oxalate (SR 33966 A) (Example 65) M.p.: about 115° C. (ethylether)

3-{4-[3-(di-n-butylamino)propoxy]benzenesulfonyl} 2-isopropyl 1,4-dimethyl indole hydrogen oxalate (SR 33974 A) (Example 66) M.p.: 72° C. (ethylether)

5-benzyloxy 2-{4-[3-(N-methyl N-3,4-dimethoxy-β-phenethylamino)propoxy]benzenesulfonyl} 3-isopropyl indole hydrogen fumarate (SR 33981 A) (Example 67) M.p.: begins to sinter at 90° C. (isopropanol)

3-isopropyl 5-methoxy 1-methyl indol-2-yl) 4-[3-(N-methyl N-3,4-dimethoxy-β-phenethylamino)propoxy]phenyl sulfoxide hydrogen fumarate (SR 33982 A) (Example 68) M.p.: begins to sinter at 85° C. (ethanol/ethylether).

2-isopropyl 1,4-dimethyl 3-{4-[3-(N-methyl N-3,4-dimethoxy-β-phenethylamino)propoxy]phenylthio}indole hydrogen fumarate (SR 33984 A) (Example 69) M.p.: begins to sinter at 90° C. (ethylether)

3-{4-[3-(N-methyl N-3,4-dimethoxy-β-phenethylamino)propoxy]benzenesulfonyl} 2-isopropyl 1,4-dimethyl indole hydrogen fumarate (SR 33976 A) (Example 70) M.p.: about 100° C.

2-{4-[3-(di-n-butylamino)propoxy]benzenesulfonyl} 1-methyl 3-isopropyl 5-chloro indole hydrochloride (SR 34040 A) (Example 71) M.p.: 148° C. (ethyl acetate/ethylether)

2-{4-[3-(N-methyl N-3,4-dimethoxy-β-phenethylamino)propoxy]benzenesulfonyl} 1-methyl 3-isopropyl 5-hydroxy indole hydrogen oxalate (SR 34028 A) (Example 72) M.p.: about 115° C. (isopropanol)

1-{4-[3-(N-methyl N-3,4-dimethoxy-β-phenethylamino)propoxy]benzenesulfonyl} 2-isopropyl 5-chloro indolizine hydrochloride (SR 34059 A) (Example 73) M.p.: 130° C. (ethyl acetate)

2-isopropyl 8-methyl 1-{4-[3-(N-methyl N-3,4-dimethoxy-β-phenethylamino)propoxy]benzenesulfonyl}indolizine hydrogen fumarate (SR 33871 A) (Example 74) M.p.: about 120° C. (ethanol)

1-{4-[3-(di-n-butylamino)propoxy]benzenesulfonyl} 2-isopropyl 8-methyl indolizine (SR 33882 A) (Example 75) M.p.: 87°-88° C. (methanol)

1-{4-[3-(N-methyl N-3,5-dimethoxy-β-phenethylamino)propoxy]benzenesulfonyl} 2-isopropyl 8-methyl indolizine a) hydrogen oxalate (SR 33919 A) (Example 76) M.p.: 157° C. (ethyl acetate, methanol, ethylether)

b) Hydrogen fumarate (SR 33919 B) (Example 77) M.p.: 139°-141° C. (decomposition)

3-{4-[3-(N-methyl N-3,4-dimethoxy-β-phenethylamino)propoxy]benezenesulfonyl} 2-ethyl 4-methyl pyrazolo[1,5-a]pyridine hydrogen oxalate (SR 33929 A) (Example 78) M.p.: 180.9° C. (methanol/ethanol 7/3)

2-Isopropyl 5-methyl 1-{4-[3-(N-methyl N-3,4-dimethoxy-β-phenethylamino)propoxy]benzenesulfonyl}indolizine.

a) Hydrogen oxalate (SR 33940 A) (Example 79) M.p.: 112°-115° C. (ethyl acetate/methanol/ethylether)

b) Hydrochloride (SR 33940 B) (Example 80) Amorphous solid

3-{4-[3-(N-methyl N-3,4-dimethoxy-β-phenethylamino)propoxy]benzenesulfonyl} 2-ethyl 6-methyl pyrazolo[1,5-a]pyridine hydrogen oxalate (SR 33954 A) (Example 81) M.p.: 140° C. (isopropanol)

1-{4-[3-(N-methyl N-3,4-dimethoxy-β-phenethylamino)propoxy]benzenesulfonyl} 2-isopropyl 6-methyl indolizine hydrogen oxalate (SR 33960 A) (Example 82) M.p.: 144°-146° C. (methyl ethyl ketone).

1-{4-[3-(N-methyl N-3,4-dimethoxy-β-phenethylamino)propoxy]benzenesulfonyl} 2-isopropyl 6-benzyloxy indolizine (SR 34060 A) (Example 83) M.p.: 73°–74° C. (methanol)

1-{4-[3-(N-methyl N-3,4-dimethoxy-β-phenethylamino)propoxy]benzenesulfonyl} 2-phenyl 8-methyl indolizine hydrochloride (SR 34050 A) (Example 84) M.p.: between 100° C. and 140° C. (decomposition).

3-{4-[3-(N-methyl N-3,4-dimethoxy-β-phenethylamino)propoxy]benzenesulfonyl} 1,2,5-trimethyl pyrrole hydrogen oxalate (SR 33997 A) (Example 85) M.p.: 165° C. (isopropanol)

3-{4-[3-(di-n-butylamino)propoxy]benzenesulfonyl} 1,2,5-trimethyl pyrrole hydrogen oxalate (SR 34020 A) (Example 86) M.p.: 94° C. (ethyl acetate)

(1,2,5-trimethyl pyrrolyl) 4-[3-(N-methyl N-3,4-dimethoxy-β-phenethylamino)propoxy]phenyl sulfoxide hydrogen oxalate (SR 34033 A) (Example 87) M.p.: 135° C. (isopropanol).

2-{4-[3-(N-methyl N-3,4-dimethoxy-β-phenethylamino)propoxy]benzenesulfonyl} 4-ethyl 3,5-dimethyl pyrrole hydrochloride (SR 34035 A) (Example 88) M.p.: about 100° C. (ethylether)

5-benzyloxy 2-{4-[3-(N-methyl N-3,4-dimethoxy-β-phenethylamino)propoxy]benzenesulfonyl} 3-isopropyl 1-[3-(N-methyl N-3,4-dimethoxy-β-phenethylamino)prop-1-yl]indole fumarate (SR 33983 A) (Example 89) M.p.: begins to sinter at 100° C.

5-chloro 2-isopropyl 3-{4-[3-(di-n-butylamino)propoxy]benzenesulfonyl} 1-methyl indole (SR 34052 A) (Example 90) M.p.: 105° C. (heptane)

2-isopropyl 8-methyl 1-[4-(3-tert-butylamino-propoxy)-benzenesulfonyl]indolizine hydrochloride (example 91) M.p.: 199°–200° C. (ethanol)

2-isopropyl 8-methyl 1-[4-(3-n-butylamino-propoxy)-benzenesulfonyl]indolizine hydrochloride (Example 92) M.p.: 165° C. (isopropanol).

2-isopropanol 8-methyl 1-{4-[3-(N-3,4,5-trimethyl-β-phenethylamino)propoxy]benzenesulfonyl}indolizine hydrogen oxalate (SR 34066 A) (Example 93) M.p.: 206° C. (methanol)

2-isopropyl 8-methyl 1-{4-[3-(N-methyl N-3,4-dimethoxy-5-methyl-β-phenethylamino)propoxy]benzenesulfonyl}indolizine citrate (Example 94) M.p.: about 50° C. (isopropanol/ethylether)

1,3,5-trimethyl 2-{4-[3-(N-methyl N-3,4-dimethoxy-β-phenethylamino)propoxy]benzenesulfonyl} 4-ethyl pyrrole hydrochloride (Example 95) 2-isopropyl 8-methyl 1-{4-[3-(N-3,4-dimethoxy-β-phenethylamino)propoxy]benzenesulfonyl}indolizine hydrogen fumarate (Example 96) Tacky product.

2-isopropyl 8-methyl 1-{4-[3-(N-methyl N-3,4-dimethoxy 5-methyl-β-phenethylamino)propoxy]benzenesulfonyl}indolizine hydrogen oxalate (Example 97) M.p.: 174°–177° C. (ethyl acetate)

We claim:

1. An aminoalkoxyphenyl compound of general formula:

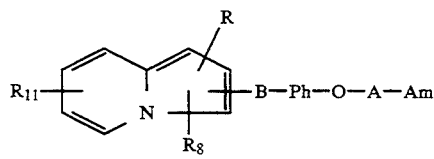

and pharmaceutically acceptable salts thereof, wherein:

B is selected from the group consisting of —S—, —SO— and —SO$_2$—;

Ph is selected from the group consisting of

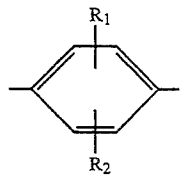

(D)

and

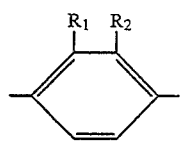

(E)

in which $R_1$ and $R_2$ are identical or different and are selected from the group consisting of hydrogen, methyl, ethyl and halogen;

A is selected from the group consisting of a straight or branched $C_2$–$C_5$ alkylene radical, a 2-hydroxypropylene radical and a 2-($C_1$–$C_4$)alkoxypropylene radical;

Am is selected from the group consisting of

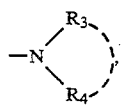

(F)

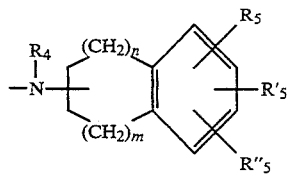

(G)

and

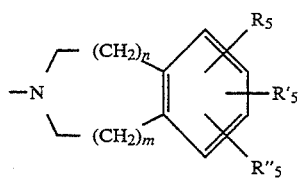

(H)

in which $R_3$ is selected from the group consisting of a $C_1$–$C_8$ alkyl, $C_3$–$C_6$ cycloalkyl and a radical of formula:

Alk—Ar in which Alk is selected from the group consisting of a single bond and a linear or branched alkylene radical having from 2 to 5 carbon atoms, and Ar is selected from the group consisting of pyridyl, phenyl, 2,3-methylenedioxyphenyl, 3,4-methylenedioxyphenyl and a phenyl substituted by one or several substituents, identical or different, selected from the group consisting of a halogen, $C_1$–$C_4$ alkyl and $C_1$–$C_4$ alkoxy, $R_4$ is selected from the group consisting of hydrogen and $C_1$–$C_8$ alkyl, or $R_3$ and $R_4$, taken together, are selected from the group consisting of an alkylene and an alkenylene radical having from 3 to 6 carbon atoms and optionally substituted by a phenyl radical or optionally interrupted by —O—, —N= or >N—$R_6$, $R_6$ being selected from the group consisting of a $C_1$–$C_4$ alkyl, $C_3$–$C_6$ cycloalkyl, phenyl optionally substituted by a radical selected from halogen, $C_1$–$C_4$ alkyl and $C_1$–$C_4$ alkoxy, $R_5$, $R'_5$ and $R''_5$, identical or different, are selected from the group consisting of hydrogen, halogen and $C_1$–$C_4$ alkyl, and n and m, identical or different, are 0, 1, 2 or 3;

R is selected from the group consisting of hydrogen, $C_1$–$C_8$ alkyl, $C_3$–$C_6$ cycloalkyl, benzyl and phenyl optionally substituted by one or several substituents, identical or different, selected from the group consisting of halogen, $C_1$–$C_4$ alkyl, $C_1$–$C_4$ alkoxy and nitro;

$R_8$ is selected from the group consisting of hydrogen, $C_1$–$C_4$ alkyl, $C_1$–$C_4$ alkoxy, halogen, hydroxy, benzyloxy, nitro, amino, ($C_1$–$C_4$ alkyl)amino, di($C_1$–$C_4$ alkyl)amino, sulfonamido, ($C_1$–$C_4$ alkyl)sulfonamido, phenylsulfonamido, cyano($C_1$–$C_4$ alkoxy)carbonyl and ($C_1$–$C_4$ alkyl)carbonyl; and $R_{11}$ is selected from the group consisting of a $C_1$–$C_4$ alkyl, halogen, hydroxy, benzyloxy, nitro, amino, ($C_1$–$C_4$ alkyl)amino, di($C_1$–$C_4$ alkyl)amino, sulfonamido, ($C_1$–$C_4$ alkyl)sulfonamido, phenylsulfonamido, cyano, ($C_1$–$C_4$ alkoxy)carbonyl and ($C_1$–$C_4$ alkyl)carbonyl.

2. An aminoalkoxyphenyl compound of general formula:

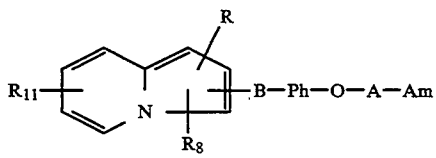

and pharmaceutically acceptable salts thereof wherein:

B is selected from the group consisting of —S—, —SO— and —SO$_2$—;

Ph is selected from the group consisting of

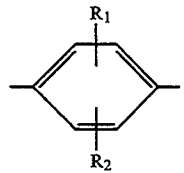

(D)

and

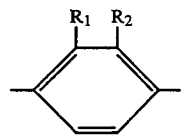

(E)

in which $R_1$ and $R_2$ are identical or different and are selected from the group consisting of hydrogen, methyl, ethyl and halogen;

A is selected from the group consisting of a straight or branched $C_2$–$C_5$ alkylene radical, a 2-hydroxypropylene radical and a 2-($C_1$–$C_4$)alkoxypropylene radical;

Am represents

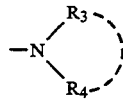

in which $R_3$ is selected from the group consisting of a $C_1$–$C_8$ alkyl, $C_3$–$C_6$ cycloalkyl and a radical of formula:

Alk—Ar in which Alk is selected from the group consisting of a single bond and a linear or branched alkylene radical having from 2 to 5 carbon atoms, and Ar is selected from the group consisting of pyridyl, phenyl, 2,3-methylenedioxyphenyl, 3,4-methylenedioxyphenyl and a phenyl substituted by one or several substituents, identical or different, selected from the group consisting of halogen, $C_1$–$C_4$ alkyl and $C_1$–$C_4$ alkoxy, $R_4$ is selected from the group consisting of hydrogen and $C_1$–$C_8$ alkyl, or $R_3$ and $R_4$, taken together, are selected from the group consisting of an alkylene and an alkenylene radical having from 3 to 6 carbon atoms and optionally substituted by a phenyl radical or optionally interrupted by —O—, —N= or >N—$R_6$, $R_6$ being selected from the group consisting of a $C_1$–$C_4$ alkyl, $C_3$–$C_6$ cycloalkyl, and phenyl optionally substituted by a radical selected from the group consisting of halogen, $C_1$–$C_4$ alkyl and $C_1$–$C_4$ alkoxy;

R is selected from the group consisting of hydrogen, $C_1$–$C_8$ alkyl, $C_3$–$C_6$ cycloalkyl, benzyl and phenyl optionally substituted by one or several substituents, identical or different, selected from the group consisting of a halogen, $C_1$–$C_4$ alkyl, $C_1$–$C_4$ alkoxy and nitro;

$R_8$ is selected from the group consisting of hydrogen, $C_1$–$C_4$ alkyl, $C_1$–$C_4$ alkoxy, halogen, hydroxy, benzyloxy, nitro, amino, ($C_1$–$C_4$ alkyl)amino, di($C_1$–$C_4$ alkyl)amino, sulfonamido, ($C_1$–$C_4$ alkyl)sulfonamido, phenylsulfonamido, cyano ($C_1$–$C_4$ alkoxy)carbonyl and ($C_1$–$C_4$ alkyl) carbonyl; and $R_{11}$ is selected from the group consisting of a $C_1$–$C_4$ alkyl, halogen, hydroxy, benzyloxy, nitro, amino, ($C_1$–$C_4$ alkyl)amino, di($C_1$–$C_4$ alkyl)amino, sulfonamido, ($C_1$–$C_4$ alkyl)sulfonamido, phenylsulfonamido, cyano, ($C_1$–$C_4$ alkoxy)carbonyl and ($C_1$–$C_4$ alkyl)carbonyl.

3. An aminoalkoxyphenyl derivative according to claim 1 or claim 2 of formula:

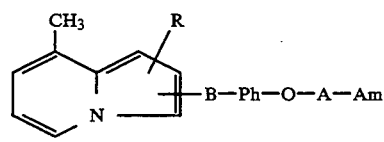

wherein R, B, Ph, A and Am are as previously defined.

4. An aminoalkoxyphenyl derivative according to claim 1 or claim 2, in which B represents an —SO$_2$— group.

5. An aminoalkoxyphenyl derivative according to claim 1 or claim 2, wherein $R_1$ and $R_2$ each is hydrogen.

6. An aminoalkoxyphenyl derivative according to claim 1 or claim 2, wherein R is selected from the group consisting of isopropyl and cyclopropyl.

7. An aminoalkoxyphenyl derivative according to claim 1 or claim 2, wherein $R_5$, $R'_5$ and $R''_5$, identical or different, are selected from the group consisting of hydrogen, chlorine, methyl and methoxy.

8. An aminoalkoxyphenyl derivative according to claim 1 or claim 2, wherein $R_3$ is said radical of formula Alk—Ar.

9. An aminoalkoxyphenyl derivative according to claim 1 or claim 2, wherein the —O—A—N$<^{R_3}_{R_4}$ chain is selected from the group consisting of (N-methyl N-3,4-dimethoxy-$\beta$-phenethylamino)propoxy and (N-methyl N-3,5-dimethoxy-$\beta$-phenethylamino)propoxy.

10. An aminoalkoxyphenyl derivative according to claim 1, wherein Ph is a group of said formula (D).

11. An aminoalkoxyphenyl derivative according to claim 1 or claim 2, wherein the pharmaceutically acceptable salt is oxalate, hydrochloride or fumarate.

12. An aminoalkoxyphenyl derivative according to claim 1, which is 2-isopropyl 8-methyl 1-{4-[3-(N-methyl N-3,5-dimethoxy-$\beta$-phenethylamino)propoxy]-benzenesulfonyl}indolozine or a pharmaceutically acceptable salt thereof.

13. An aminoalkoxyphenyl derivative according to claim 1, which is 2-isopropyl 8-methyl 1-{4-[3-(N-methyl N-3,4-dimethoxy-$\beta$-phenethylamino)propoxy]-benzenesulfonyl}indolozine or a pharmaceutically acceptable salt thereof.

14. An aminoalkoxyphenyl derivative according to claim 1, which is 1-{4-[3-(di-n-butylamino)propoxy]-benzene-sulfonyl}-2-isopropyl 8-methyl indolizine or a pharmaceutically acceptable salt thereof.

15. An aminoalkoxyphenyl derivative according to claim 1, which is 2-isopropyl 8-methyl 1-{4-[3-(6,7-dimethoxy 1,2,3,4-tetrahydro isoquinolin-2-yl)propoxy]benzene-sulfonyl}indolizine or a pharmaceutically acceptable salt thereof.

16. An aminoalkoxyphenyl derivative according to claim 1, which is 2-isopropyl 5-methyl 1-{4-[3-(N-methyl N-3,4-dimethoxy-$\beta$-phenethylamino)propoxy]-benzenesulfonyl}indolizine or a pharmaceutically acceptable salt thereof.

17. A pharmaceutical or veterinary composition containing, as an active ingredient, at least one aminoalkoxyphenyl derivative according to claim 1, in combination with a pharmaceutical vehicle or an excipient therefor.

18. A pharmaceutical or veterinary composition containing, as an active ingredient, at least one aminoalkoxyphenyl derivative according to claim 2, in combination with a pharmaceutical vehicle or an excipient therefor.

19. A pharmaceutical or veterinary composition according to claim 17 for the treatment of pathological syndromes of the cardiovascular system containing from 50 mg to 500 mg of said active ingredient.

20. A method for the treatment of pathological syndromes of the cardiovascular system in a host in need of such treatment comprising the administration to said host of an effective amount of an aminoalkoxyphenyl compound according to claim 1 or claim 2.

21. A method for the treatment of ocular diseases in a host in need of such treatment comprising the administration to said host of an effective amount of an aminoalkoxyphenyl compound according to claim 1 or claim 2.

22. An aminoalkoxyphenyl compound of general formula:

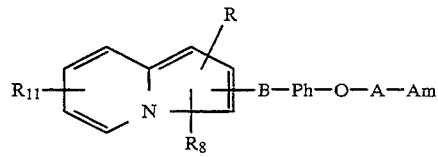

or a pharmaceutically acceptable salt thereof, wherein:

B is selected from the group consisting of —S—, —SO— and —SO$_2$—;

Ph is selected from the group consisting of

and

in which $R_1$ and $R_2$ are identical or different and are selected from the group consisting of hydrogen, methyl, ethyl and halogen;

A is selected from the group consisting of a straight or branched $C_2$-$C_5$ alkylene radical, a 2-hydroxypropylene radical and a 2-($C_1$-$C_4$)alkoxypropylene radical;

Am is selected from the group consisting of

and

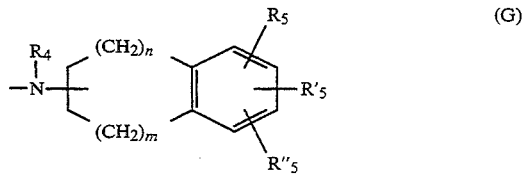

in which $R_3$ is selected from the group consisting of a $C_1$-$C_8$ alkyl, $C_3$-$C_6$ cycloalkyl and a radical of the formula:

Alk—Ar in which Alk is selected from the group consisting of a single bond and a linear or branched alkylene radical having from 2 to 5 carbon atoms, and Ar is selected from the group consisting of pyridyl, phenyl, 2,3-methylenedioxyphenyl, 3,4-methylenedioxyphenyl and a phenyl substituted by one or several substituents, identical or different, selected from the group consisting of a halogen, $C_1$–$C_4$ alkyl and $C_1$–$C_4$ alkoxy, $R_4$ is selected from the group consisting of hydrogen and $C_1$–$C_8$ alkyl, $R_5$, $R'_5$ and $R''_5$, identical or different, are selected from the group consisting of hydrogen, halogen and $C_1$–$C_4$ alkyl, and n and m, identical or different, are 0 or 1;

R is selected from the group consisting of hydrogen, $C_1$–$C_8$ alkyl, $C_3$–$C_6$ cycloalkyl, benzyl and phenyl optionally substituted by one or several substituents, identical or different, selected from the group consisting of halogen, $C_1$–$C_4$ alkyl, $C_1$–$C_4$ alkoxy and nitro;

$R_8$ is selected from the group consisting of hydrogen, $C_1$–$C_4$ alkyl, $C_1$–$C_4$ alkoxy, halogen, hydroxy, benzyloxy, nitro, amino, ($C_1$–$C_4$ alkyl)amino, di($C_1$–$C_6$ alkyl)amino, sulfonamido, ($C_1$–$C_4$ alkyl)sulfonamido, phenylsulfonamido, cyano, ($C_1$–$C_4$ alkoxy)carbonyl and ($C_1$–$C_4$ alkyl)carbonyl; and $R_{11}$ is selected from the group consisting of $C_1$–$C_4$ alkyl, halogen, hydroxy, benzyloxy, nitro, amino, ($C_1$–$C_4$ alkyl)amino, di($C_1$–$C_4$ alkyl)amino, sulfonamido, ($C_1$–$C_4$ alkyl)sulfonamido, phenylsulfonamido, cyano, ($C_1$–$C_4$ alkoxy)carbonyl and ($C_1$–$C_4$ alkyl)carbonyl.

* * * * *